United States Patent
Yamaguchi et al.

(10) Patent No.: US 10,388,891 B2
(45) Date of Patent: Aug. 20, 2019

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Tomoya Yamaguchi, Kanagawa (JP); Hideko Inoue, Kanagawa (JP); Tatsuyoshi Takahashi, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 15/085,390

(22) Filed: Mar. 30, 2016

(65) Prior Publication Data
US 2016/0293863 A1 Oct. 6, 2016

(30) Foreign Application Priority Data
Apr. 1, 2015 (JP) .................................. 2015-074799

(51) Int. Cl.
*C07F 15/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01); (Continued)

(58) Field of Classification Search
CPC .. C07F 9/587; C07F 15/06; C09K 2211/1029; C09K 2211/1044; C09K 2211/187
See application file for complete search history.

(56) References Cited

U.S. PATENT DOCUMENTS 6,097,147 A 8/2000 Baldo et al.
6,803,720 B2 10/2004 Kwong et al.
(Continued)

FOREIGN PATENT DOCUMENTS

JP 2007-137872 A 6/2007
JP 2008-069221 A 3/2008
(Continued)

OTHER PUBLICATIONS

Accession No. (AN):17126900 Lin. Struct. Formula (LSF):Hg(C10H50N2(NHNH2))C12, dated Oct. 17, 2008.
(Continued)

*Primary Examiner* — Shane Fang
(74) *Attorney, Agent, or Firm* — Husch Blackwell LLP

(57) ABSTRACT

As a novel substance having a novel skeleton, an organometallic complex with high emission efficiency is provided. The organometallic complex includes a metal and a ligand. The metal is iridium or platinum. The ligand includes a 5H-pyrimido[5,4-b]indole skeleton and an aryl group bonded to the 4-position of the 5H-pyrimido[5,4-b]indole skeleton. The 3-position of the 5H-pyrimido[5,4-b]indole skeleton and the aryl group are bonded to the metal. In the formula, M represents iridium or platinum. In addition, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

18 Claims, 22 Drawing Sheets

(51) Int. Cl.
 *H01L 51/00* (2006.01)
 *H05B 33/14* (2006.01)
(52) U.S. Cl.
 CPC ...... *H05B 33/14* (2013.01); *C09K 2211/1007* (2013.01); *C09K 2211/1059* (2013.01); *C09K 2211/185* (2013.01); *H01L 2251/308* (2013.01)

(56) References Cited

U.S. PATENT DOCUMENTS

| | | | |
|---|---|---|---|
| 6,830,828 | B2 | 12/2004 | Thompson et al. |
| 6,902,830 | B2 | 6/2005 | Thompson et al. |
| 6,953,628 | B2 | 10/2005 | Kamatani et al. |
| 7,001,536 | B2 | 2/2006 | Thompson et al. |
| 7,220,495 | B2 | 5/2007 | Tsuboyama et al. |
| 7,291,406 | B2 | 11/2007 | Thompson et al. |
| 7,537,844 | B2 | 5/2009 | Thompson et al. |
| 7,589,203 | B2 | 9/2009 | Stossel et al. |
| 7,807,839 | B2 | 10/2010 | Inoue et al. |
| 7,883,787 | B2 | 2/2011 | Thompson et al. |
| 7,955,716 | B2 | 6/2011 | Nomura et al. |
| 7,960,038 | B2 | 6/2011 | Ohsawa et al. |
| 7,993,494 | B2 | 8/2011 | Inoue et al. |
| 8,084,145 | B2 | 12/2011 | Inoue et al. |
| 8,164,090 | B2 | 4/2012 | Iwasaki et al. |
| 2002/0063516 | A1 | 5/2002 | Tsuboyama et al. |
| 2005/0221123 | A1 | 10/2005 | Inoue et al. |
| 2006/0127696 | A1 | 6/2006 | Stossel et al. |
| 2007/0128466 | A1 | 6/2007 | Nomura et al. |
| 2007/0129545 | A1 | 6/2007 | Inoue et al. |
| 2007/0244320 | A1 | 10/2007 | Inoue et al. |
| 2008/0149923 | A1 | 6/2008 | Ohsawa et al. |
| 2008/0233432 | A1 | 9/2008 | Inoue et al. |
| 2008/0286604 | A1 | 11/2008 | Inoue et al. |
| 2008/0305361 | A1 | 12/2008 | Inoue et al. |
| 2008/0312437 | A1 | 12/2008 | Inoue et al. |
| 2009/0015143 | A1 | 1/2009 | Inoue et al. |
| 2009/0033209 | A1 | 2/2009 | Seo et al. |
| 2009/0039776 | A1 | 2/2009 | Yamada et al. |
| 2010/0105902 | A1 | 4/2010 | Inoue et al. |
| 2010/0145044 | A1 | 6/2010 | Inoue et al. |
| 2010/0181905 | A1 | 7/2010 | Inoue et al. |
| 2010/0219407 | A1 | 9/2010 | Kamatani et al. |
| 2011/0082296 | A1 | 4/2011 | Inoue et al. |
| 2011/0112296 | A1 | 5/2011 | Thompson et al. |
| 2011/0187265 | A1 | 8/2011 | De Cola et al. |
| 2011/0210316 | A1 | 9/2011 | Kadoma et al. |
| 2011/0245495 | A1 | 10/2011 | Inoue et al. |
| 2011/0309345 | A1 | 12/2011 | Balaganesan et al. |
| 2012/0061707 | A1 | 3/2012 | Seo et al. |
| 2012/0098417 | A1 | 4/2012 | Inoue et al. |
| 2012/0104373 | A1 | 5/2012 | Inoue et al. |
| 2012/0193613 | A1 | 8/2012 | Kadoma et al. |
| 2012/0197020 | A1 | 8/2012 | Osaka et al. |
| 2012/0205632 | A1 | 8/2012 | Shitagaki et al. |
| 2012/0205687 | A1 | 8/2012 | Yamazaki et al. |
| 2012/0206035 | A1 | 8/2012 | Shitagaki et al. |
| 2012/0208999 | A1 | 8/2012 | Konno |
| 2012/0217487 | A1 | 8/2012 | Yamazaki et al. |
| 2012/0242219 | A1 | 9/2012 | Seo et al. |
| 2012/0248421 | A1 | 10/2012 | Yamazaki et al. |
| 2012/0256535 | A1 | 10/2012 | Seo et al. |
| 2012/0264936 | A1 | 10/2012 | Inoue et al. |
| 2012/0274201 | A1 | 11/2012 | Seo et al. |
| 2012/0277427 | A1 | 11/2012 | Inoue et al. |
| 2013/0165653 | A1 | 6/2013 | Inoue et al. |
| 2013/0324721 | A1 | 12/2013 | Inoue et al. |
| 2015/0236276 | A1* | 8/2015 | Boudreault ......... H01L 51/0085 257/40 |

FOREIGN PATENT DOCUMENTS

| | | |
|---|---|---|
| JP | 2015-083560 A | 4/2015 |
| WO | WO 2008/035664 A1 | 3/2008 |

OTHER PUBLICATIONS

Accession No. (AN):18070774 Chemical Name (CN):(4-methoxybenzofuro<3, 2-d>pyrimidino)cadmium(II) chloride Lin. Struct. Formula (LSF):Cd (C6H40C4HN20CH3)C12, dated Oct. 22, 2018.

Accession No. (AN):17126600 Lin. Struct. Forrnula (LSF):Co(C10H50N2(NHNH2))C12, dated Oct. 17, 2008.

Accession No. (AN):18070840 Chemical Name (CN):(4-ethoxybenzofuro<3, 2-d>pyrimidino)zinc(II) chloride Lin. Struct. Formula (LSF):Zn(C6H40C4HN20C2H5) C12, dated Oct. 22, 2008.

* cited by examiner

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organometallic complex, particularly, to an organometallic complex capable of converting triplet excitation energy into light emission. In addition, one embodiment of the present invention relates to a light-emitting element, a light-emitting device, an electronic device, and a lighting device each including the organometallic complex.

Note that one embodiment of the present invention is not limited to the above technical field. The technical field of one embodiment of the present invention disclosed in this specification and the like relates to an object, a substance, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a power storage device, a memory device, an imaging device, a method of driving any of them, a method of manufacturing any of them, and the like.

2. Description of the Related Art

In recent years, research and development have been extensively conducted on light-emitting elements using electroluminescence (EL). In the basic structure of such a light-emitting element, a layer containing a light-emitting substance (an EL layer) is interposed between a pair of electrodes. By applying a voltage to this element, light emission from the light-emitting substance can be obtained.

Since the above light-emitting element is a self-luminous type, a display device using this light-emitting element has advantages such as high visibility, no necessity of a backlight, and low power consumption. Furthermore, such a light-emitting element also has advantages in that, for example, it can be formed to be thin and lightweight and has high response speed.

In the case of an organic EL element in which an EL layer containing an organometallic complex as a light-emitting substance is provided between a pair of electrodes, application of a voltage between the pair of electrodes causes injection of electrons from a cathode and holes from an anode into the EL layer having a light-emitting property, and thus, a current flows. By recombination of the injected electrons and holes, the organometallic complex is raised to an excited state to provide light emission.

The excited state of the organometallic complex can be a singlet excited state ($S_1$) or a triplet excited state ($T_1$), and light emission from the singlet excited state is referred to as fluorescence and light emission from the triplet excited state is referred to as phosphorescence. The statistical generation ratio thereof in the light-emitting element is considered to be $S_1:T_1=1:3$.

Among the organometallic complexes, a compound capable of converting singlet excitation energy into light emission is called a fluorescent compound (fluorescent material), and a compound capable of converting triplet excitation energy into light emission is called a phosphorescent compound (phosphorescent material).

The internal quantum efficiency (the ratio of the number of generated photons to the number of injected carriers) of a light-emitting element including a fluorescent material is thought to have a theoretical limit of 25%, on the basis of $S_1:T_1=1:3$, while the internal quantum efficiency of a light-emitting element including a phosphorescent material is thought to have a theoretical limit of 75%.

In other words, a light-emitting element including a phosphorescent material has higher emission efficiency than a light-emitting element including a fluorescent material. Therefore, a phosphorescent material capable of converting triplet excitation energy into light emission has been actively developed in recent years. An organometallic complex that contains iridium or the like as a central metal is particularly attracting attention because of its high phosphorescence quantum yield (see Patent Documents 1 to 3, for example).

REFERENCES

Patent Documents

[Patent Document 1] Japanese Published Patent Application No. 2007-137872
[Patent Document 2] Japanese Published Patent Application No. 2008-069221
[Patent Document 3] PCT International Publication No. 2008-035664

SUMMARY OF THE INVENTION

Although phosphorescent materials exhibiting various emission colors have been developed as disclosed in Patent Documents 1 to 3, not many red light-emitting materials with excellent emission efficiency have been reported so far.

In view of the above, according to one embodiment of the present invention, a novel organometallic complex capable of emitting phosphorescence is provided. A novel organometallic complex capable of emitting red phosphorescence is provided. A novel organometallic complex with high emission efficiency is provided. A light-emitting element, a light-emitting device, an electronic device, or a lighting device including the novel organometallic complex is provided.

A light-emitting element, a light-emitting device, an electronic device, or a lighting device with high emission efficiency is provided. A light-emitting element, a light-emitting device, an electronic device, or a lighting device with high reliability is provided. A light-emitting element, a light-emitting device, an electronic device, or a lighting device with low power consumption is provided. A novel light-emitting element, light-emitting device, electronic device, or lighting device is provided.

Note that the description of these objects does not preclude the existence of other objects. In one embodiment of the present invention, there is no need to achieve all the objects. Other objects will be apparent from and can be derived from the description of the specification, the drawings, the claims, and the like.

One embodiment of the present invention is an organometallic complex including a metal and a ligand. The ligand includes a 5H-pyrimido[5,4-b]indole skeleton and an aryl group bonded to the 4-position of the 5H-pyrimido[5,4-b]indole skeleton. The metal is iridium or platinum. The 3-position of the 5H-pyrimido[5,4-b]indole skeleton and the aryl group are bonded to the metal.

Another embodiment of the present invention is an organometallic complex including a metal, a first ligand, and a second ligand. The first ligand includes a 5H-pyrimido[5,4-b]indole skeleton and an aryl group bonded to the 4-position of the 5H-pyrimido[5,4-b]indole skeleton. The second ligand is a monoanionic bidentate chelate ligand having a β-diketone structure, a carboxyl group, a phenolic hydroxyl group, or a structure in which two coordinating elements are both nitrogen. The metal is iridium or platinum. The 3-position of the 5H-pyrimido[5,4-b]indole skeleton and the aryl group that are included in the first ligand are bonded to the metal. The second ligand is bonded to the metal.

Another embodiment of the present invention is an organometallic complex including a structure represented by the following general formula (G1).

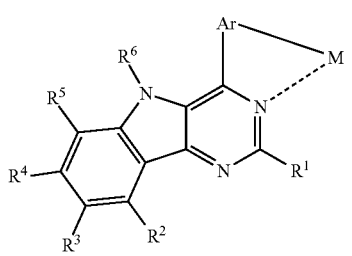
(G1)

In the general formula (G1), M represents iridium or platinum. In addition, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

Another embodiment of the present invention is an organometallic complex represented by the following general formula (G2).

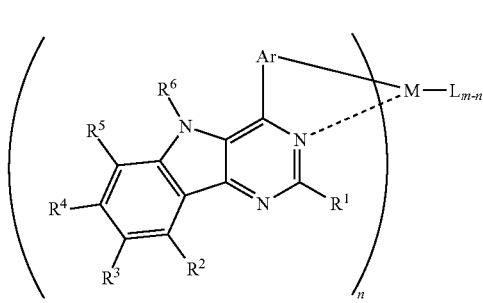
(G2)

In the general formula (G2), M represents iridium or platinum, and L represents a monoanionic ligand. In addition, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms. When M represents iridium, m is 3 and n is 2 or 3. When M represents platinum, m is 2 and n is 1 or 2.

In the general formula (G2), the monoanionic ligand is preferably a monoanionic bidentate chelate ligand having a β-diketone structure, a carboxyl group, a phenolic hydroxyl group, or a structure in which two coordinating elements are both nitrogen. A monoanionic bidentate chelate ligand having a β-diketone structure is particularly preferable because the β-diketone structure allows the organometallic complex to have higher solubility in an organic solvent and to be easily purified. The β-diketone structure is preferably included for realization of an organometallic complex with high emission efficiency. Furthermore, the β-diketone structure brings advantages such as a higher sublimation property and excellent evaporativity.

In each of the above-described structures, the monoanionic ligand is preferably represented by any of general formulae (L1) to (L7). These ligands are useful because they have high coordinative ability and are available at low price.

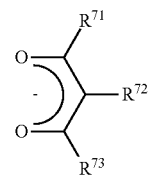
(L1)

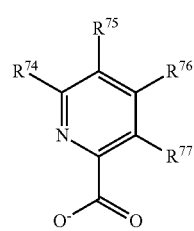
(L2)

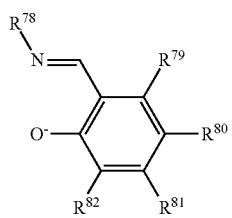
(L3)

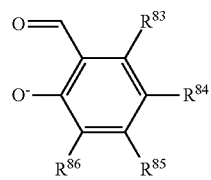
(L4)

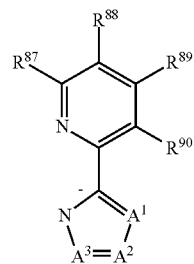
(L5)

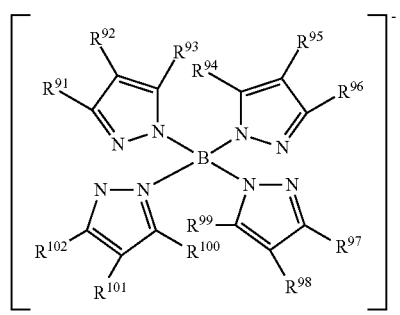
(L6)

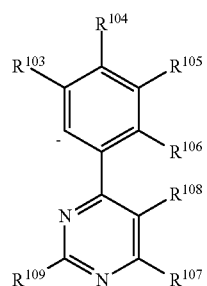

(L7)

In the formulae, each of $R^{71}$ to $R^{109}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. Each of $A^1$ to $A^3$ independently represents nitrogen, carbon bonded to hydrogen, or carbon having a substituent. The substituent is an alkyl group having 1 to 6 carbon atoms, a halogen group, a haloalkyl group having 1 to 6 carbon atoms, or a phenyl group.

Another embodiment of the present invention is an organometallic complex represented by the following general formula (G3).

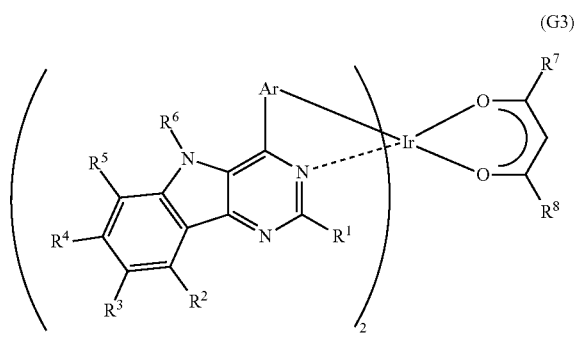

(G3)

In the general formula (G3), Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms. Each of $R^7$ and $R^8$ independently represents hydrogen or a substituted or unsubstituted alkyl group having 1 to 6 carbon atoms.

Another embodiment of the present invention is an organometallic complex represented by the following general formula (G4).

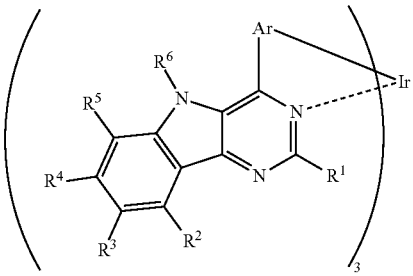

(G4)

In the general formula (G4), Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

In the above general formulae (G1) to (G4), specific examples of the alkyl group having 1 to 6 carbon atoms which is represented by any of $R^1$ to $R^6$ are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and the like. Specific examples of the aryl group having 6 to 10 carbon atoms which is represented by any of $R^1$ to $R^6$ are a phenyl group, a biphenyl group, and the like. Specific examples of the aryl group having 6 to 13 carbon atoms which is represented by Ar are a phenyl group, a biphenyl group, a naphthyl group, a fluorenyl group, and the like.

Another embodiment of the present invention is an organometallic complex represented by the following structural formula (100).

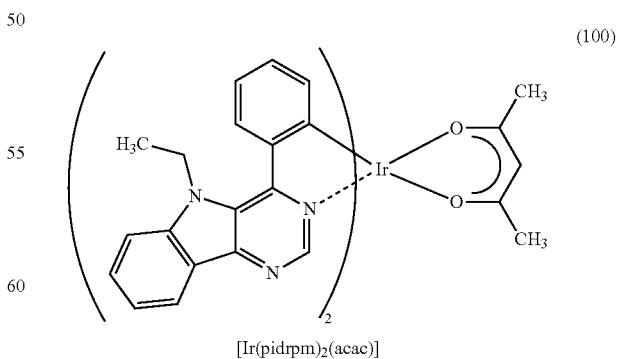

(100)

[Ir(pidrpm)₂(acac)]

Another embodiment of the present invention is an organometallic complex represented by the following structural formula (127).

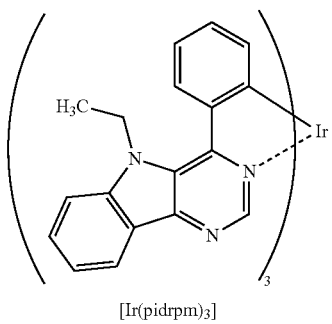

[Ir(pidrpm)₃]

The organometallic complex which is one embodiment of the present invention is a very effective organometallic complex for the following reason: the organometallic complex can emit phosphorescence, that is, provide luminescence from a triplet excited state, and therefore higher efficiency is possible when the organometallic complex is used in a light-emitting element. Thus, one embodiment of the present invention also includes a light-emitting element using the organometallic complex which is one embodiment of the present invention.

In addition, one embodiment of the present invention includes, in its category, not only a light-emitting device including a light-emitting element but also an electronic device and a lighting device each including a light-emitting device. Thus, a light-emitting device in this specification refers to an image display device or a light source (e.g., a lighting device). In addition, a light-emitting device includes, in its category, a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

With one embodiment of the present invention, it is possible to provide a novel organometallic complex capable of emitting phosphorescence, a novel organometallic complex capable of emitting red phosphorescence, a novel organometallic complex with high emission efficiency, or a light-emitting element, a light-emitting device, an electronic device, or a lighting device including the novel organometallic complex.

It is possible to provide a light-emitting element, a light-emitting device, an electronic device, or a lighting device with high emission efficiency, high reliability, or low power consumption. It is possible to provide a novel organometallic complex. It is possible to provide a novel light-emitting element, light-emitting device, electronic device, or lighting device.

DETAILED DESCRIPTION OF THE INVENTION

Figure 1A:
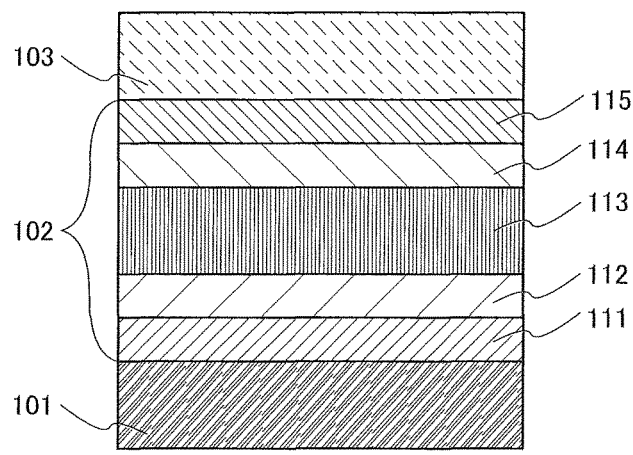
FIGS. 1A and 1B each illustrate a structure of a light-emitting element.

Embodiments of the present invention will be described in detail below with reference to the drawings. Note that the present invention is not limited to the following description, and modes and details thereof can be variously modified without departing from the spirit and the scope of the present invention. Accordingly, the present invention should not be interpreted as being limited to the content of the embodiments and examples below.

Embodiment 1

In this embodiment, an organometallic complex which is one embodiment of the present invention is described.

An organometallic complex which is one embodiment of the present invention includes a metal and a ligand. The ligand includes a 5H-pyrimido[5,4-b]indole skeleton and an aryl group bonded to the 4-position of the 5H-pyrimido[5,4-b]indole skeleton. The metal is iridium or platinum. The 3-position of the 5H-pyrimido[5,4-b]indole skeleton and the aryl group are bonded to the metal. One mode of the organometallic complex described in this embodiment includes a structure represented by the general formula (G1).

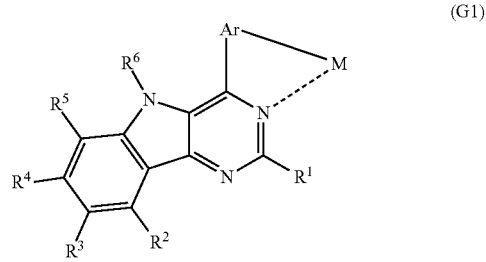

In the general formula (G1), M represents iridium or platinum, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

Another mode of the organometallic complex described in this embodiment is represented by the general formula (G2).

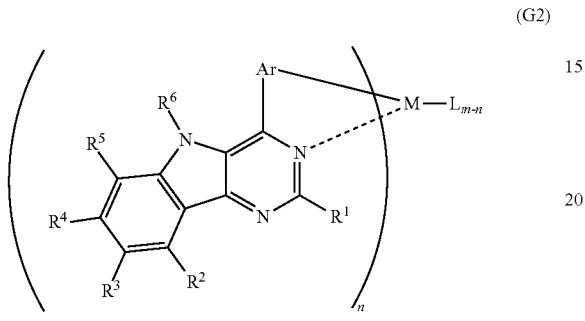

(G2)

In the general formula (G2), M represents iridium or platinum, and L represents a monoanionic ligand. In addition, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms. When M represents iridium, m is 3 and n is 2 or 3. When M represents platinum, m is 2 and n is 1 or 2.

In the general formula (G2), the monoanionic ligand is preferably a monoanionic bidentate chelate ligand having a β-diketone structure, a carboxyl group, a phenolic hydroxyl group, or a structure in which two coordinating elements are both nitrogen. A monoanionic bidentate chelate ligand having a β-diketone structure is particularly preferable.

Specifically, the monoanionic ligand is preferably represented by any of general formulae (L1) to (L7).

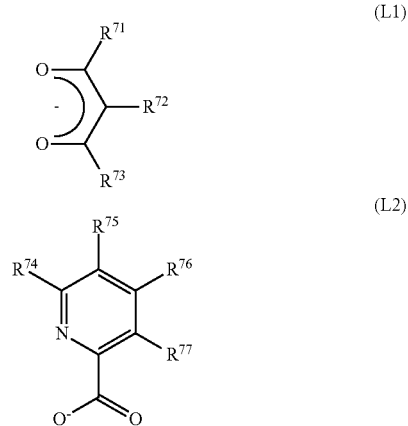

(L1)

(L2)

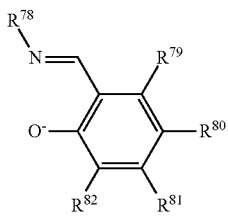

(L3)

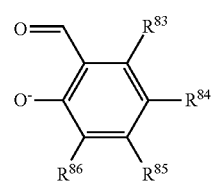

(L4)

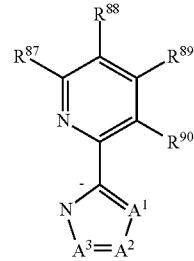

(L5)

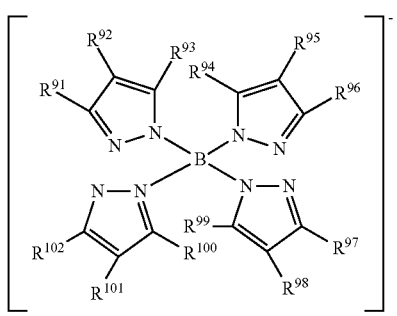

(L6)

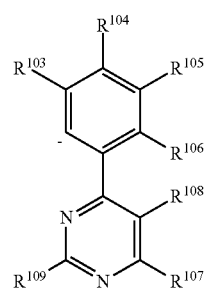

(L7)

In the formulae, each of $R^{71}$ to $R^{109}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms. Each of $A^1$ to $A^3$ independently represents nitrogen, carbon bonded to hydrogen, or carbon having a substituent. The substituent in this case is an alkyl group having 1 to 6 carbon atoms, a halogen group, a haloalkyl group having 1 to 6 carbon atoms, or a phenyl group.

In the above general formulae (G1) and (G2), specific examples of the alkyl group having 1 to 6 carbon atoms which is represented by any of $R^1$ to $R^6$ are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and the like. Specific examples of the aryl group having 6 to 10 carbon atoms which is represented by any of $R^1$ to $R^6$ are a phenyl group, a biphenyl group, and the like. Specific examples of the aryl group having 6 to 13 carbon atoms which is represented by Ar are a phenyl group, a biphenyl group, a naphthyl group, a fluorenyl group, and the like.

Note that the organometallic complex which is one embodiment of the present invention has a 5H-pyrimido[5,4-b]indole skeleton in which an indole ring and a pyrimidine ring are fused. Such a structure in which an indole ring and a pyrimidine ring are fused can improve the heat resistance of the organometallic complex, leading to improved reliability of a light-emitting element using the organometallic iridium complex. Because the pyrimidine ring enhances emission efficiency, the organometallic complex which is one embodiment of the present invention offers a red-light-emitting material with high emission efficiency.

Next, specific structural formulae of the above-described organometallic complex which is one embodiment of the present invention are shown (the following structural formulae (100) to (135)). Note that the present invention is not limited thereto.

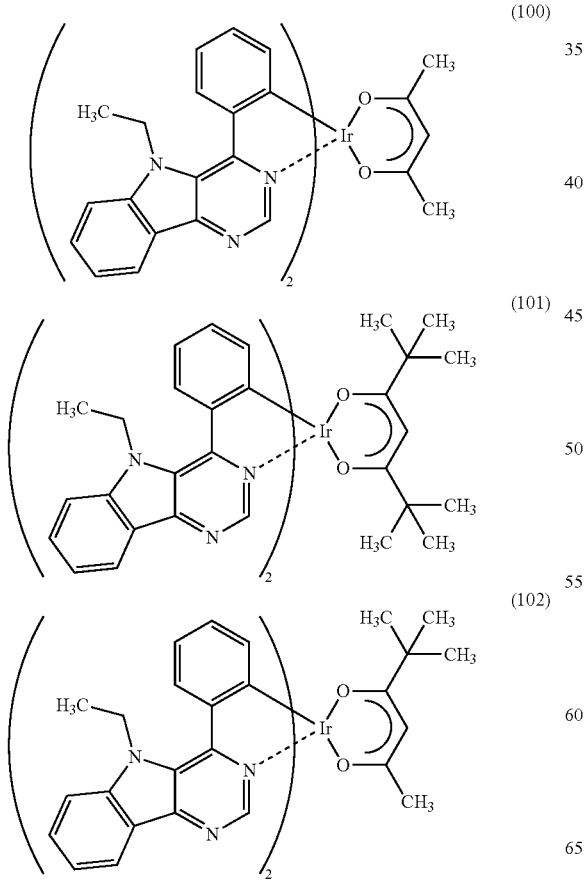

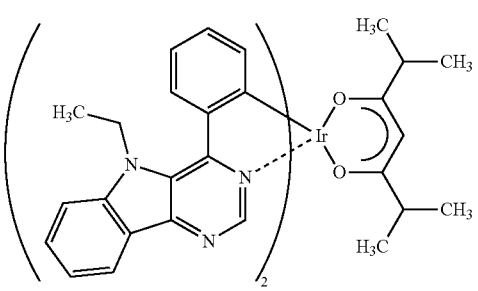

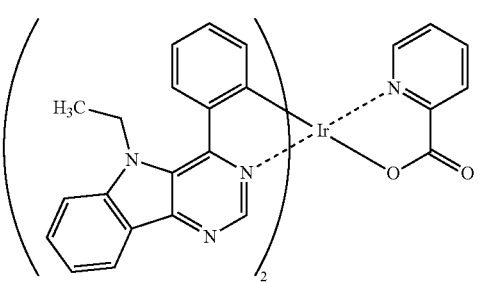

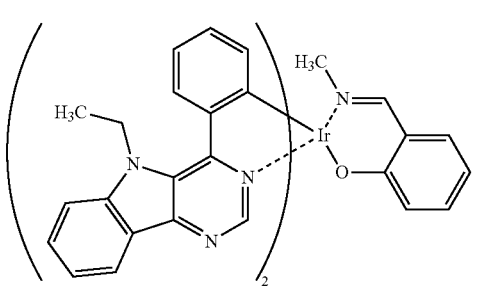

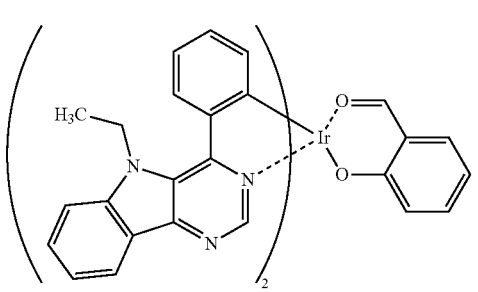

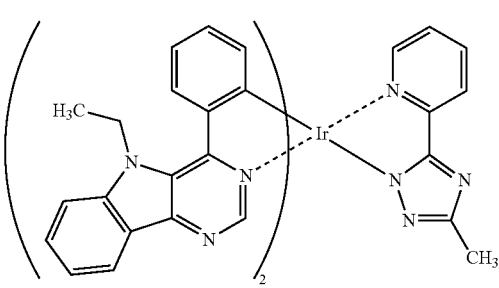

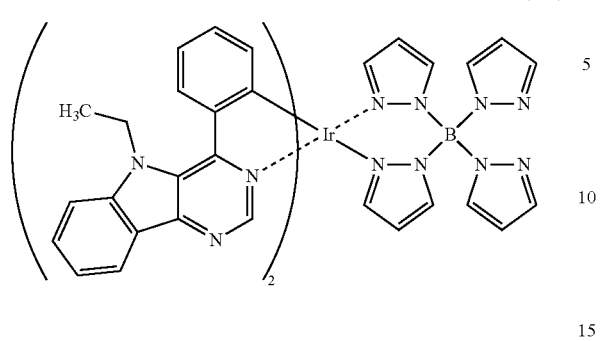
(108)
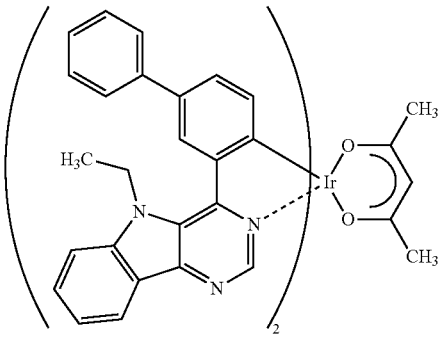
(113)
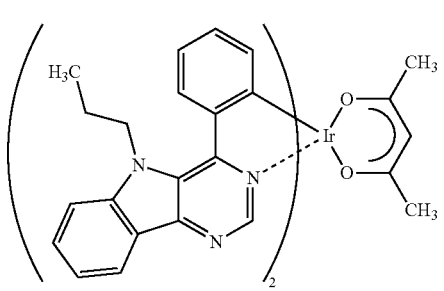
(109)
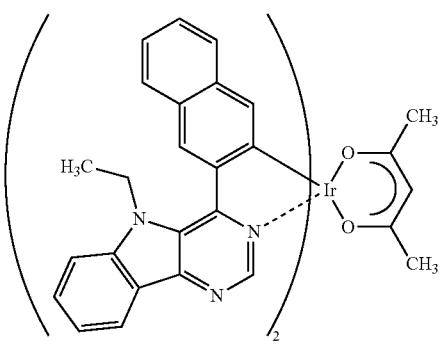
(114)
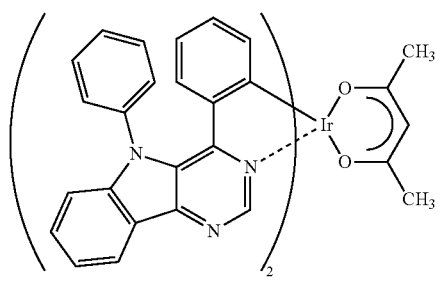
(110)
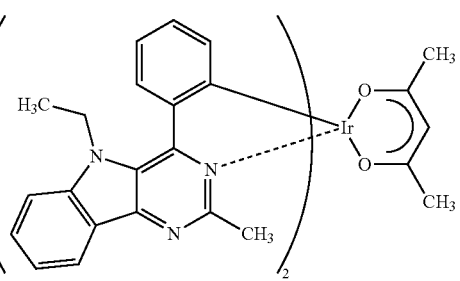
(115)
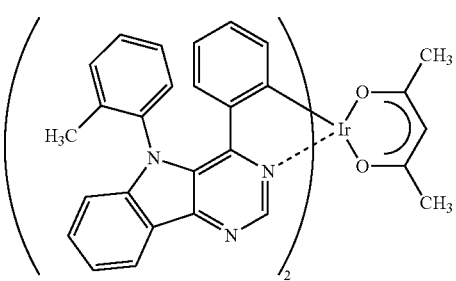
(111)
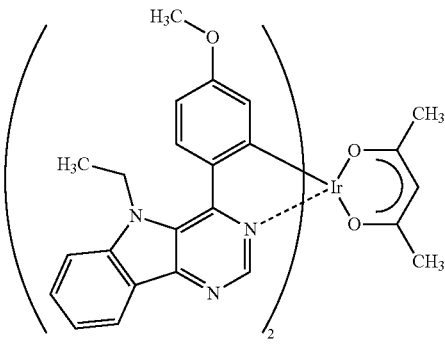
(116)
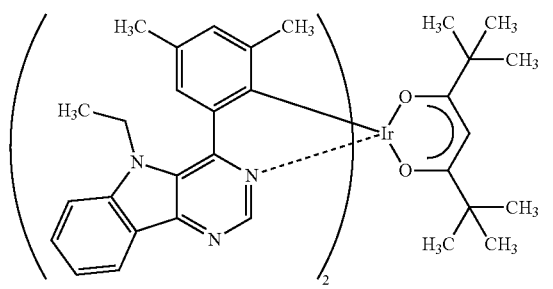
(112)
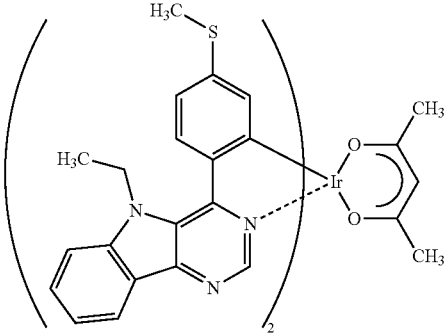
(117)

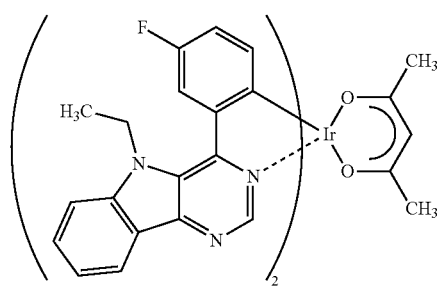
(118)
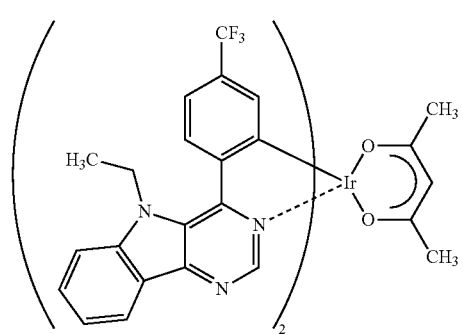
(119)
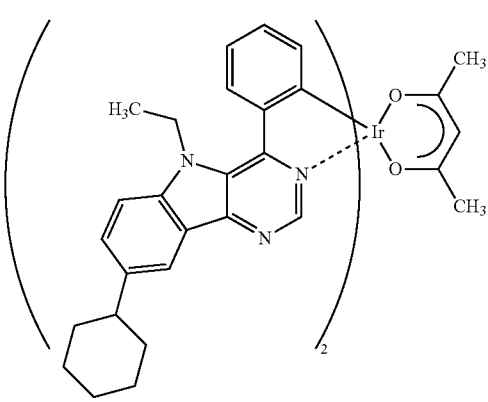
(120)
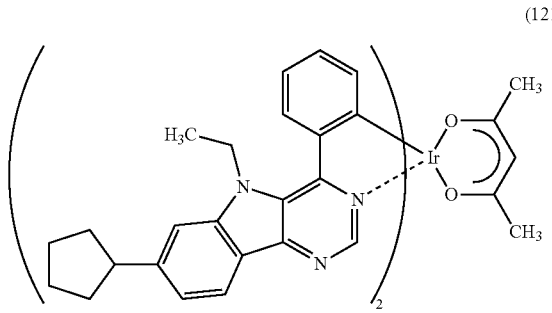
(121)
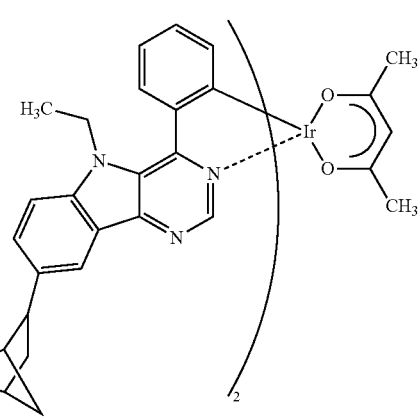
(122)
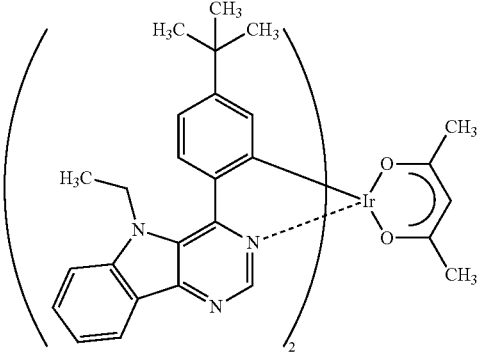
(123)
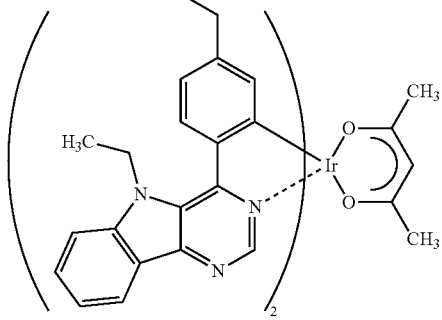
(124)
(125)

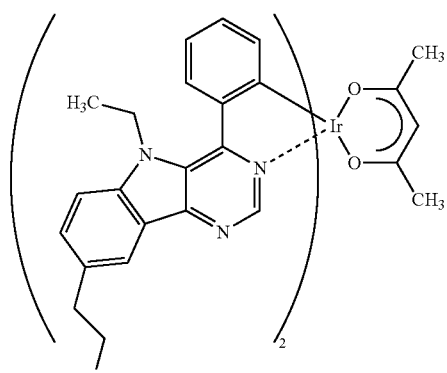
(126)

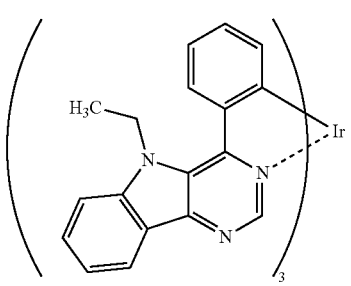
(127)

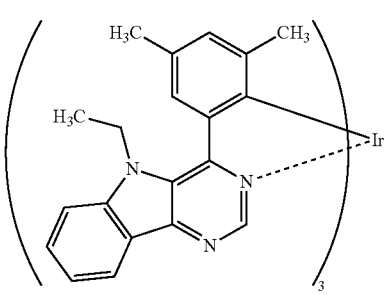
(128)

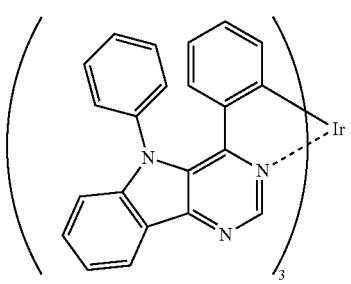
(129)

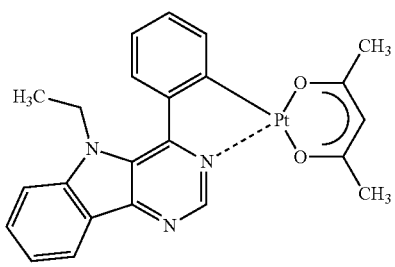
(130)

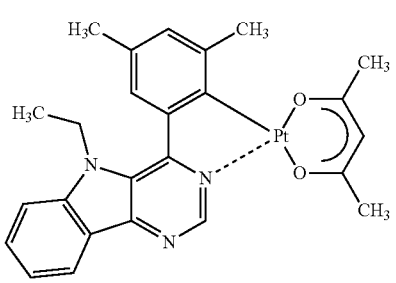
(131)

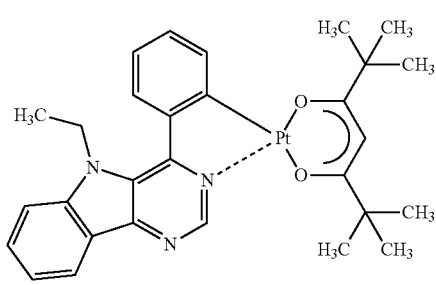
(132)

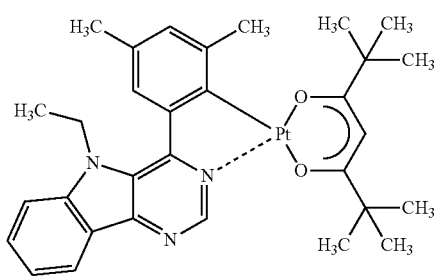
(133)

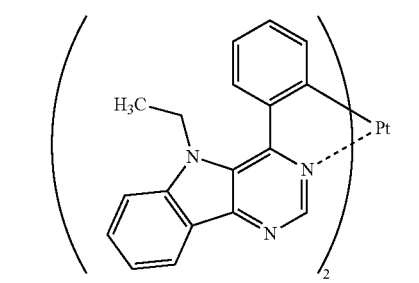
(134)

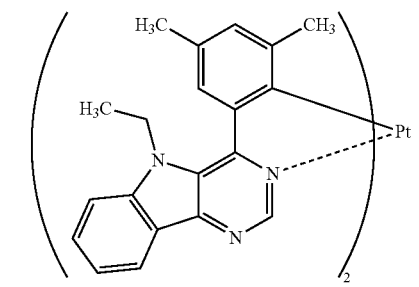
(135)

The organometallic complexes represented by the structural formulae (100) to (135) are novel substances capable of emitting phosphorescence. Note that there can be stereoisomers of these substances depending on the type of the ligand. The organometallic complex which is one embodiment of the present invention includes all of these isomers.

Next, an example of a method of synthesizing the organometallic complex represented by the above general formula (G2) is described.

Method of Synthesizing 4-arylpyrimido[5,4-b]indole Derivative Represented by General Formula (G0)

An example of a method of synthesizing a 4-arylpyrimido[5,4-b]indole derivative represented by a general formula (G0) below is described. The 4-arylpyrimido[5,4-b]indole derivative represented by the general formula (G0) below can be synthesized by any of simple synthesis schemes (a), (a'), and (a''), as described below.

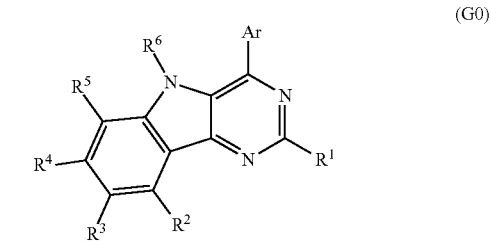

In the general formula (G0), Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

For example, as illustrated in the synthesis scheme (a), a halogenated pyrimidine compound (A1) is coupled with arylboronic acid (A2), whereby the 4-arylpyrimido[5,4-b]indole derivative represented by the general formula (G0) can be obtained.

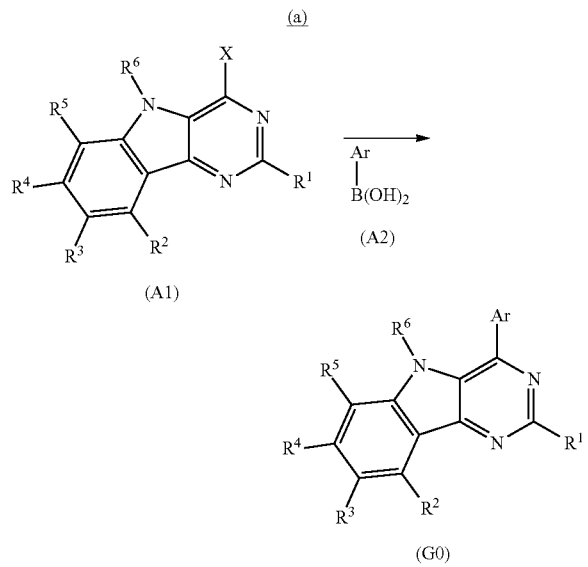

In the synthesis scheme (a), X represents a halogen, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

Alternatively, as illustrated in the synthesis scheme (a'), hydrogen of a pyrimido[5,4-b]indole compound (A1') is abstracted by a strong base such as sodium hydride, potassium carbonate, or butyllithium, and after a salt is produced, the salt is reacted with a halogen-containing compound (A2'), whereby the 4-arylpyrimido[5,4-b]indole derivative represented by the general formula (G0) can be obtained. Further alternatively, as illustrated in the synthesis scheme (a''), an Ullmann reaction, a Buchwald reaction, or the like between the pyrimido[5,4-b]indole compound (A1') and the halogen-containing compound (A2') can be used.

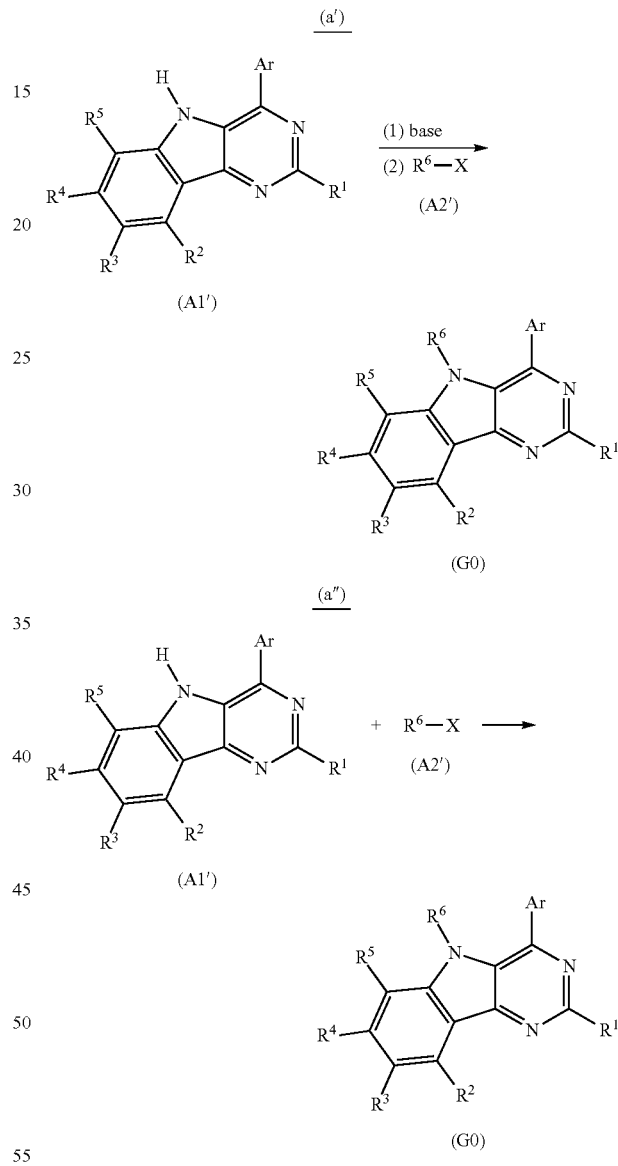

In the synthesis schemes (a) and (a'), X represents a halogen, Ar represents a substituted or unsubstituted aryl group having 6 to 13 carbon atoms, and each of $R^1$ to $R^6$ independently represents hydrogen, a substituted or unsubstituted alkyl group having 1 to 6 carbon atoms, or a substituted or unsubstituted aryl group having 6 to 10 carbon atoms.

Since various kinds of the above-described compounds (A1), (A2), (A1'), and (A2') are commercially available or can be synthesized, many kinds of the 4-arylpyrimido[5,4-b]indole derivatives represented by the general formula (G0) can be synthesized. Thus, the organometallic complex which is one embodiment of the present invention has wide variations of ligands.

Method of Synthesizing Organometallic Complex which is One Embodiment of the Present Invention and Represented by General Formula (G2)

The organometallic complex which is one embodiment of the present invention and represented by the general formula (G2) can be synthesized as shown in a synthesis scheme (b-1) below. The 4-arylpyrimido[5,4-b]indole derivative represented by the general formula (G0) and a compound of iridium or platinum which contains a halogen (e.g., iridium chloride, iridium bromide, iridium iodide, or potassium tetrachloroplatinate) are heated in an inert gas atmosphere using no solvent, an alcohol-based solvent (e.g., glycerol, ethylene glycol, 2-methoxyethanol, or 2-ethoxyethanol) alone, or a mixed solvent of water and one or more of the alcohol-based solvents, so that a dinuclear complex (B), which is one type of an organometallic complex including a halogen-bridged structure and is a novel substance, can be obtained. There is no particular limitation on a heating means, and an oil bath, a sand bath, or an aluminum block may be used. Alternatively, microwaves can be used as a heating means.

In the synthesis scheme (b-1), X represents a halogen, Ar represents a substituted or unsubstituted aryl group having 6 to 13 carbon atoms, each of $R^1$ to $R^6$ independently represents hydrogen, a substituted or unsubstituted alkyl group having 1 to 6 carbon atoms, or a substituted or unsubstituted aryl group having 6 to 10 carbon atoms, and M represents iridium or platinum. When M represents iridium, n is 2. When M represents platinum, n is 1.

Then, as shown in a synthesis scheme (b-2), the dinuclear complex (B) obtained in the synthesis scheme (b-1) and HL which is a material of a monoanionic ligand are reacted in an inert gas atmosphere, so that a proton of HL is separated and L coordinates to the central metal M. Thus, the organometallic complex which is one embodiment of the present invention and represented by the general formula (G2) can be obtained. There is no particular limitation on a heating means, and an oil bath, a sand bath, or an aluminum block may be used. Alternatively, microwaves can be used as a heating means.

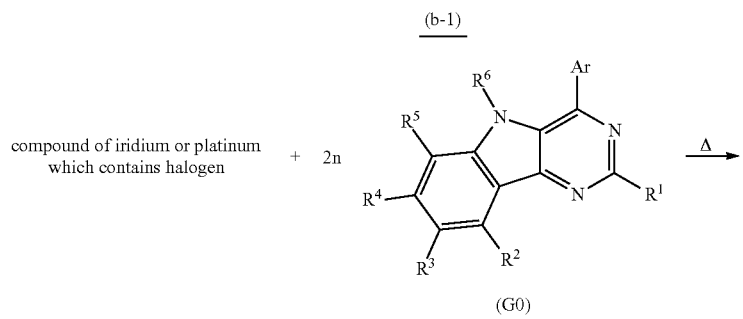

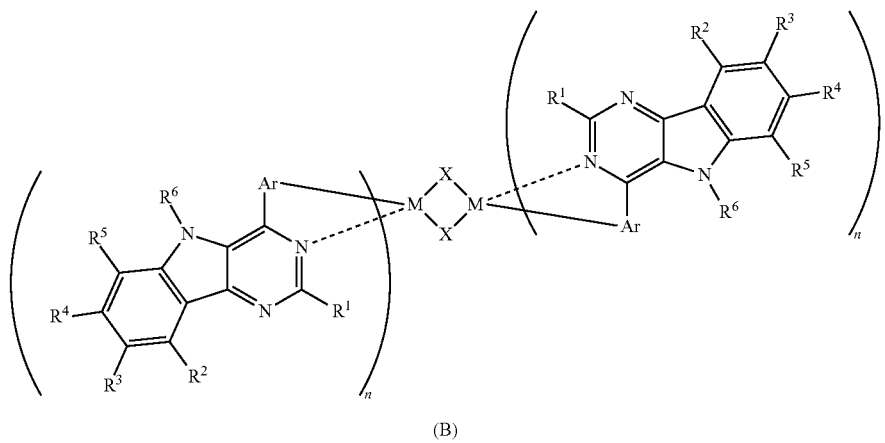

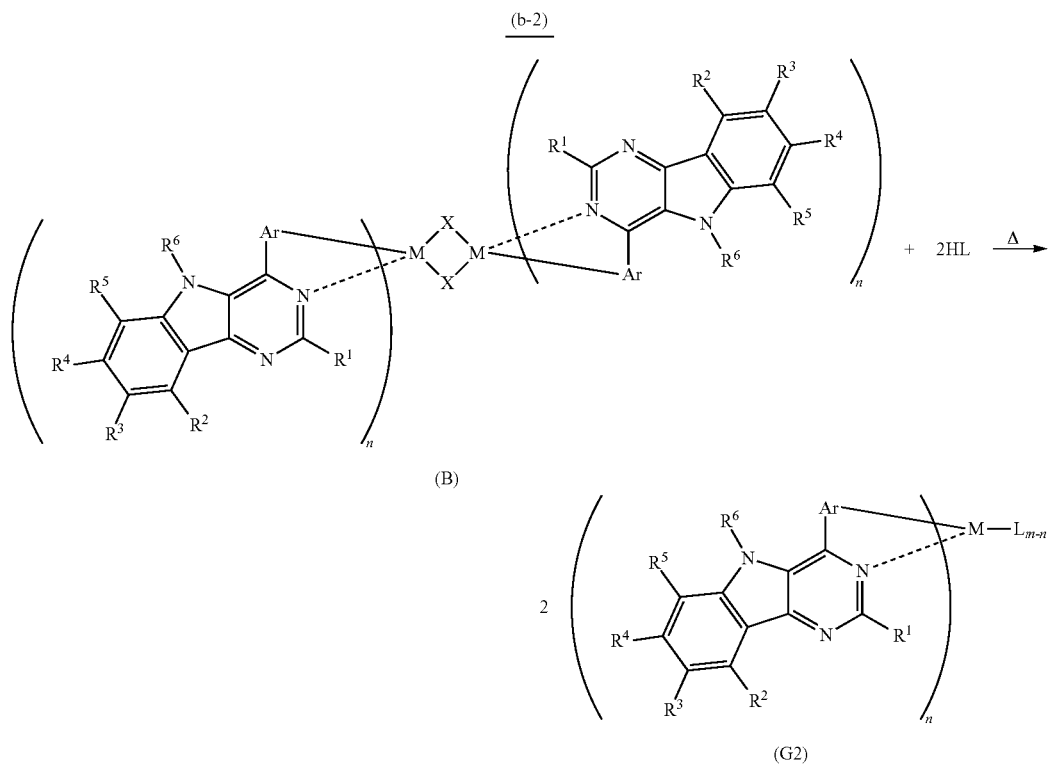

(B)

(G2)

In the synthesis scheme (b-2), L represents a monoanionic ligand, X represents a halogen, Ar represents a substituted or unsubstituted aryl group having 6 to 13 carbon atoms, each of $R^1$ to $R^6$ independently represents hydrogen, a substituted or unsubstituted alkyl group having 1 to 6 carbon atoms, or a substituted or unsubstituted aryl group having 6 to 10 carbon atoms, and M represents iridium or platinum. When M represents iridium, m is 3 and n is 2 or 3. When M represents platinum, m is 2 and n is 1 or 2.

An organometallic complex which is one embodiment of the present invention and represented by a general formula (G2') can be synthesized according to a synthesis scheme (c) shown below. The 4-arylpyrimido[5,4-b]indole derivative represented by the general formula (G0) is mixed with a compound of iridium or platinum which contains a halogen (e.g., iridium chloride, iridium bromide, iridium iodide, or potassium tetrachloroplatinate) or with an organometallic complex compound of iridium or platinum (e.g., an acetylacetonate complex or a diethylsulfide complex), and the mixture is then heated, whereby the organometallic complex represented by the general formula (G2') can be obtained. This heating process may be performed after dissolving the 4-arylpyrimido[5,4-b]indole derivative represented by the general formula (G0) and the compound of iridium or platinum which contains a halogen or the organometallic complex compound of iridium or platinum in an alcohol-based solvent (e.g., glycerol, ethylene glycol, 2-methoxyethanol, or 2-ethoxyethanol). There is no particular limitation on a heating means, and an oil bath, a sand bath, or an aluminum block may be used. Alternatively, microwaves can be used as a heating means.

(c)

compound of iridium or platinum which contains halogen or + organometallic complex compound of iridium or platinum

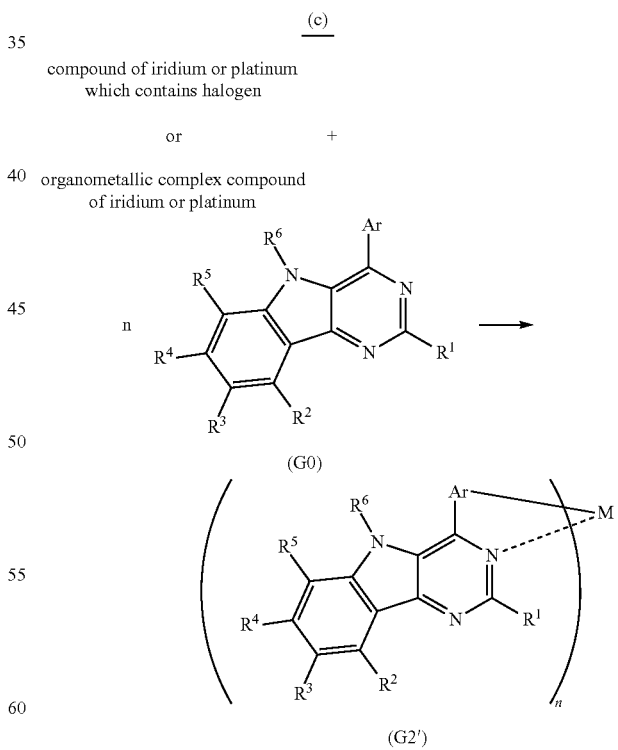

(G0)

(G2')

In the synthesis scheme (c), Ar represents a substituted or unsubstituted aryl group having 6 to 13 carbon atoms, each of $R^1$ to $R^6$ independently represents hydrogen, a substituted or unsubstituted alkyl group having 1 to 6 carbon atoms, or a substituted or unsubstituted aryl group having 6 to 10 carbon atoms, and M represents iridium or platinum. When M represents iridium, n is 3. When M represents platinum, n is 2.

The above is the description of examples of a method of synthesizing the organometallic complex which is one embodiment of the present invention; however, the present invention is not limited thereto, and any other synthesis methods may be employed.

The above-described organometallic complex which is one embodiment of the present invention can emit phosphorescence and can be used as a light-emitting material or a light-emitting substance of a light-emitting element.

With the use of the organometallic complex which is one embodiment of the present invention, a light-emitting element, a light-emitting device, an electronic device, or a lighting device with high emission efficiency can be obtained. Alternatively, it is possible to obtain a light-emitting element, a light-emitting device, an electronic device, or a lighting device with low power consumption.

The structure described in this embodiment can be combined as appropriate with any of the structures described in other embodiments.

Embodiment 2

In this embodiment, a light-emitting element in which the organometallic complex described in Embodiment 1 is used for a light-emitting layer is described as one embodiment of the present invention with reference to FIG. 1A.

FIG. 1A illustrates a light-emitting element including an EL between a first electrode 101 and a second electrode 103. The EL layer 102 includes a light-emitting layer 113, and the light-emitting layer 113 contains the organometallic complex described in Embodiment 1. The EL layer 102 includes, in addition to the light-emitting layer 113, a hole-injection layer 111, a hole-transport layer 112, an electron-transport layer 114, and an electron-injection layer 115.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. In this manner, the organometallic complex which is one embodiment of the present invention functions as a light-emitting substance in the light-emitting element. Note that in the light-emitting element described in this embodiment, the first electrode 101 and the second electrode 103 function as an anode and a cathode, respectively.

A specific example in which the light-emitting element described in this embodiment is fabricated is described below.

Since the first electrode 101 functions as the anode, the first electrode 101 is preferably formed using any of metals, alloys, electrically conductive compounds with a high work function (specifically, a work function of 4.0 eV or more), mixtures thereof, and the like. Specific examples are indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like. Such electrically conductive metal oxide films are usually formed by a sputtering method, but may be formed by application of a sol-gel method or the like. Other examples are gold (Au), platinum (Pt), nickel (Ni), tungsten (W), chromium (Cr), molybdenum (Mo), iron (Fe), cobalt (Co), copper (Cu), palladium (Pd), titanium (Ti), silver (Ag), aluminum (Al), nitrides of metal materials (e.g., titanium nitride), and the like. Graphene can also be used. Note that when a composite material described later is used for a layer that is in contact with the first electrode 101 in the EL layer 102, an electrode material can be selected for the first electrode 101 regardless of its work function.

The hole-injection layer 111 has a function of reducing a barrier to hole injection from the first electrode 101 so that hole injection can be promoted, and the layer is a layer containing a substance having a high hole-injection property, for example, a transition metal oxide, a phthalocyanine derivative, or an aromatic amine. As a transition metal oxide, molybdenum oxide, vanadium oxide, ruthenium oxide, tungsten oxide, manganese oxide, and the like can be given. As a phthalocyanine derivative, phthalocyanine (abbreviation: $H_2Pc$), copper phthalocyanine (CuPc), and the like can be given. As an aromatic amine, 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'-biphenyl]-4,4'-diamine (abbreviation: DNTPD), and the like can be given. The hole-injection layer 111 can also be formed using a high molecule such as poly(3,4-ethylenedioxythiophene)/poly(styrenesulfonate) (PEDOT/PSS), or the like.

Alternatively, a composite material in which a substance having a hole-transport property contains a substance having an acceptor property (electron acceptor) can be used for the hole-injection layer 111. When electrons are extracted from the substance having a hole-transport property by the substance having an acceptor property, holes are generated and injected from the hole-injection layer 111 into the light-emitting layer 113 through the hole-transport layer 112. Note that the use of a substance having a hole-transport property which contains a substance having an acceptor property enables selection of a material used to form an electrode regardless of its work function. In other words, besides a material having a high work function, a material having a low work function can also be used for the first electrode 101. Examples of the substance having an acceptor property include compounds having an electron-withdrawing group (a halogen group or a cyano group) such as 7,7,8,8-tetracyano-2,3,5,6-tetrafluoroquinodimethane (abbreviation: $F_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of hetero atoms, like HAT-CN, is thermally stable and preferable. In addition, transition metal oxides can be given. Oxides of the metals that belong to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable in that their electron-accepting property is high. Among these oxides, molybdenum oxide is particularly preferable in that it is stable in the air, has a low hygroscopic property, and is easy to handle.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ $cm^2/Vs$ or more is preferably used. Organic compounds that can be used as the substance having a hole-transport property in the composite material are specifically given below.

Examples of the aromatic amine compounds are N,N'-di (p-tolyl)-N,N'-diphenyl-p-phenylenediamine (abbreviation: DTDPPA), DPAB, DNTPD, 1,3,5-tris[N-(4-diphenylaminophenyl)-N-phenylamino]benzene (abbreviation: DPA3B), and the like.

Examples of carbazole derivatives that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of carbazole derivatives that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons that can be used for the composite material are 2-test-butyl-9,10-di(2-naphthyl) anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di (2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1 \times 10^{-6}$ cm$^2$/Vs or more and which has 14 to 42 carbon atoms is particularly preferable.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

By providing a hole-injection layer, a high hole-injection property can be achieved to allow a light-emitting element to be driven at a low voltage.

Note that the hole-injection layer may be formed of only the above-described substance having an acceptor property. In this case, the substance having an acceptor property extracts electrons from the hole-transport layer, so that holes can be injected into the hole-transport layer. The substance having an acceptor property transfers the extracted electrons to the anode.

The hole-transport layer 112 is a layer containing a substance having a hole-transport property. Examples of the substance having a hole-transport property are aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(N,N-diphenylamino) triphenylamine (abbreviation: MATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP). The substances mentioned here are mainly ones that have a hole mobility of $10^{-6}$ cm$^2$/Vs or more. An organic compound given as an example of the substance having a hole-transport property in the above-described composite material for the hole-injection layer 111 can also be used for the hole-transport layer 112. However, other substances may also be used as long as their hole-transport properties are higher than their electron-transport properties. A high molecular compound such as PVK and PVTPA can also be used. Note that the layer that contains the substance having a hole-transport property is not limited to a single layer, and may be a stack of two or more layers including any of the above substances.

The light-emitting layer 113 is a layer containing a light-emitting substance. Note that the organometallic complex described in Embodiment 1 can be used as the light-emitting substance, and the light-emitting layer 113 may contain, as a host material, a substance having higher triplet excitation energy than the organometallic complex (guest material). Alternatively, the light-emitting layer 113 may contain, in addition to the light-emitting substance, two kinds of organic compounds that can form an excited complex (also called an exciplex) at the time of recombination of carriers (electrons and holes) in the light-emitting layer (the two kinds of organic compounds may be any of host materials as described above).

Examples of an organic compound that can be used as the host material and the two kinds of organic compounds that can form an exciplex include compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl) triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris (8-quinolinolato)aluminum (abbreviation: Alq$_3$). In addition, a high molecular compound such as PVK can be used.

In the case where the light-emitting layer 113 contains the organometallic complex (guest material) and the above-described host material or the above-described two kinds of organic compounds that can form an exciplex, phosphorescence can be emitted from the light-emitting layer 113 with high efficiency.

Figure 1B:
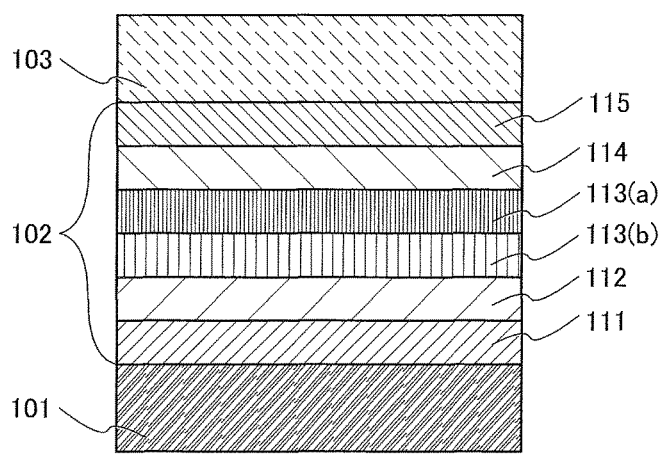

The light-emitting layer 113 does not necessarily have a single-layer structure shown in FIG. 1A and may have a stacked-layer structure including two or more layers as shown in FIG. 1B. Alternatively, the light-emitting layer 113 may contain, in addition to the organometallic complex which is one embodiment of the present invention, a light-emitting substance converting singlet excitation energy into light emission or a light-emitting substance converting triplet excitation energy into light emission. In that case, the light-emitting substance may be contained in the same layer as or in a different layer from the organometallic complex. When these light-emitting substances emit light of different colors, the light-emitting element can emit light of a desired color as a whole. For example, a light-emitting element including three light-emitting layers can emit white light as a whole, when the emission color of a first light-emitting layer is red, the emission color of a second light-emitting layer is green, and the emission color of a third light-emitting layer is blue. For example, in the case of a light-emitting element having two light-emitting layers, the emission colors of first and second light-emitting layers are complementary, so that the light-emitting element can emit white light as a whole. Note that "complementary colors" refer to colors that can produce an achromatic color when mixed. In other words, when light of complementary colors is mixed, white light emission can be obtained. Described below are examples of the light-emitting substance.

As an example of the light-emitting substance converting singlet excitation energy into light emission, a substance which emits fluorescence (a fluorescent compound) can be given.

Examples of the substance which emits fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N''-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl] N,N',N''-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into light emission include a substance which emits phosphorescence (a phosphorescent compound) and a thermally activated delayed fluorescent (TADF) material. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance which emits phosphorescence include bis{2-[3',5'-bis(trifluoromethyl)phenyl]pyridinato-N,$C^{2'}$}iridium(III) picolinate (abbreviation: [Ir(CF$_3$ppy)$_2$(pic)]), bis[2-(4',6'-difluorophenyl)pyridinato-N,$C^{2'}$]iridium(III) acetylacetonate (abbreviation: FIracac), tris(2-phenylpyridinato)iridium(III) (abbreviation: [Ir(ppy)$_3$]), bis(2-phenylpyridinato)iridium(III) acetylacetonate (abbreviation: [Ir(ppy)$_2$(acac)]), tris(acetylacetonato)(monophenanthroline)terbium(III) (abbreviation: [Tb(acac)$_3$(Phen)]), bis(benzo[h]quinolinato)iridium(III) acetylacetonate (abbreviation: [Ir(bzq)$_2$(acac)]), bis(2,4-diphenyl-1,3-oxazolato-N,$C^{2'}$)iridium(III) acetylacetonate (abbreviation: [Ir(dpo)$_2$(acac)]), bis{2-[4'-(perfluorophenyl)phenyl]pyridinato-N,$C^{2'}$}iridium(III) acetylacetonate (abbreviation: [Ir(p-PF-ph)$_2$(acac)]), bis(2-phenylbenzothiazolato-N,$C^{2'}$)iridium(III) acetylacetonate (abbreviation: [Ir(bt)$_2$(acac)]), bis[2-(2'-benzo[4,5-a]thienyl)pyridinato-N,$C^{3'}$]iridium(III) acetylacetonate (abbreviation: [Ir(btp)$_2$(acac)]), bis(1-phenylisoquinolinato-N,$C^{2'}$)iridium(III) acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato) (monophenanthroline)europium(III) (abbreviation: [Eu(DBM)$_3$(Phen)]), and tris[1-(2-thenoyl)-3,3,3-trifluoroacetonato](monophenanthroline)europium(III) (abbreviation: [Eu(TTA)$_3$(Phen)]).

Examples of the TADF material include fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). In addition, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a substance in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the $S_1$ level and the $T_1$ level becomes small.

The electron-transport layer 114 is a layer containing a substance having a high electron-transport property (also referred to as an electron-transport compound). For the electron-transport layer 114, $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$) can be used. Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4''-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl) stilbene (abbreviation: BzOs). Further alternatively, it is possible to use a high molecular compound such as poly(2, 5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances described here are mainly substances having an electron mobility of $10^{-6}$ cm$^2$/Vs or higher. However, other substances may also be used for the electron-transport layer 114 as long as their electron-transport properties are higher than their hole-transport properties.

The electron-transport layer 114 is not limited to a single layer and may be a stack of two or more layers each containing any of the substances listed above.

The electron-injection layer 115 has a function of reducing a barrier to electron injection from the second electrode 103 so that electron injection can be promoted, and the layer is a layer containing a substance having a high electron-injection property, for example, a metal belonging to Group 1 or 2 of the periodic table, or an oxide, a halide, or a carbonate of the metal. Specifically, a compound such as lithium fluoride (LiF), cesium fluoride (CsF), calcium fluoride ($CaF_2$), or lithium oxide ($LiO_x$) can be used. Alternatively, a rare earth metal compound such as erbium fluoride ($ErF_3$) can be used. An electride may also be used for the electron-injection layer 115. Examples of the electride include a substance in which electrons are added at high concentration to calcium oxide-aluminum oxide. Alternatively, a composite material containing the above-described electron-transport material and a material having an electron-donating property can also be used. As a material having an electron-donating property, a metal belonging to Group 1 or 2 of the periodic table, an oxide of the metal, and the like can be given. Any of the substances for forming the electron-transport layer 114, which are given above, can also be used.

Alternatively, the electron-injection layer 115 may be formed using a composite material in which an organic compound and a substance having a donor property (an electron donor) are mixed. The composite material is superior in an electron-injection property and an electron-transport property, since electrons are generated in the organic compound with the substance having a donor property. In that case, the organic compound is preferably a material which is excellent in transporting the generated electrons. Specifically, the above-described substances for forming the electron-transport layer 114 (e.g., a metal complex or a heteroaromatic compound) can be used. As the substance having a donor property, a substance showing an electron-donating property with respect to the organic compound may be used. Specifically, a metal belonging to Group 1 or 2 of the periodic table and a rare earth metal are preferable, and lithium, cesium, magnesium, calcium, erbium, ytterbium, or the like can be used. Furthermore, an alkali metal oxide or an alkaline earth metal oxide is preferable, and for example, lithium oxide, calcium oxide, barium oxide, or the like can be used. Alternatively, Lewis base such as magnesium oxide can be used. An organic compound such as tetrathiafulvalene (abbreviation: TTF) can also be used.

The hole-injection layer 111, the hole-transport layer 112, the light-emitting layer 113, the electron-transport layer 114, and the electron-injection layer 115, which are described above, can each be formed by any of the following methods: an evaporation method (including a vacuum evaporation method), a printing method (such as a relief printing method, an intaglio printing method, a gravure printing method, a planography printing method, or a stencil printing method), an inkjet method, a coating method, and the like.

As a substance used to form the second electrode 103, any of metals, alloys, electrically conductive compounds, and mixtures thereof which have a low work function (specifically, a work function of 3.8 eV or less) or the like can be used. Specific examples of such a cathode material are alkali metals such as lithium (Li) and cesium (Cs), metals belonging to Group 2 of the periodic table such as magnesium (Mg), calcium (Ca), and strontium (Sr), alloys containing any of these metals (e.g., MgAg and AlLi), rare earth metals such as europium (Eu) and ytterbium (Yb), alloys containing any of these metals, and the like. However, when the electron-injection layer is provided between the second electrode 103 and the electron-transport layer, for the second electrode 103, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. A wet method using a sol-gel method, or by a wet method using paste of a metal material may be employed.

In the above light-emitting element, a current flows due to a potential difference between the first electrode 101 and the second electrode 103, and holes and electrons recombine in the EL layer 102, so that light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic complex and thus can have higher efficiency than a light-emitting element including only a fluorescent compound.

Note that the light-emitting element described in this embodiment is an example of a light-emitting element fabricated using the organometallic complex which is one embodiment of the present invention. As a light-emitting device including the above-described light-emitting element, a passive matrix light-emitting device, an active matrix light-emitting device, a light-emitting device having a microcavity (micro-optical resonator) structure, or the like can be fabricated. Each of the light-emitting devices is one embodiment of the present invention.

In the case of fabricating an active matrix light-emitting device, there is no particular limitation on the structure of a transistor (TFT). For example, a staggered TFT or an inverted staggered TFT can be used as appropriate. A driver circuit formed over a TFT substrate may be formed using both an n-type TFT and a p-type TFT or only either an n-type TFT or a p-type TFT. Furthermore, there is no particular limitation on the crystallinity of a semiconductor film used for the TFT. For example, either an amorphous semiconductor film or a crystalline semiconductor film can be used. Examples of a semiconductor material include semiconductors belonging to Group 13 of the periodic table, semiconductors belonging to Group 14 of the periodic table (e.g., silicon), compound semiconductors, oxide semiconductors, and organic semiconductors.

Note that the structure described in this embodiment can be used in combination with any of the structures described in the other embodiments, as appropriate.

Embodiment 3

Described in this embodiment is a light-emitting element (hereinafter referred to as a tandem light-emitting element) with a structure in which the organometallic complex which is one embodiment of the present invention is used as an EL material in an EL layer and a plurality of EL layers are provided with a charge-generation layer provided therebetween.

Figure 2A:
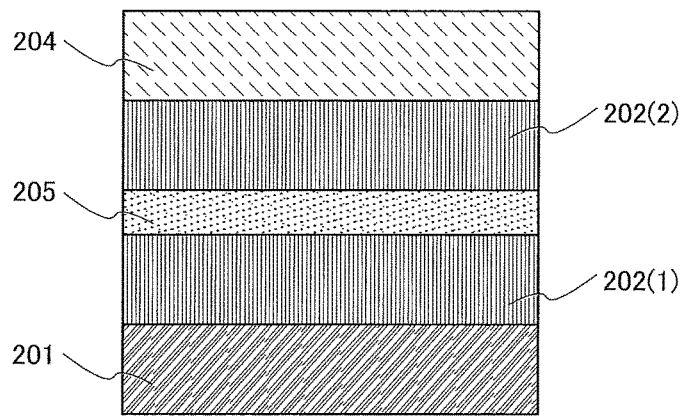
FIGS. 2A and 2B each illustrate a structure of a light-emitting element.

The light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode and the second electrode 204 functions as a cathode. Note that the first electrode 201 and the second electrode 204 can each have a structure similar to that described in Embodiment 2. In addition, one or both of the plurality of EL layers (the first EL layer 202(1) and the second EL layer 202(2)) may have a structure similar to that described in Embodiment 2. In other words, the structures of the first EL layer 202(1) and the second EL layer 202(2) may be the same or different from each other and can be similar to that described in Embodiment 2.

A charge-generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when a voltage is applied to the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which a substance having an acceptor property is added to an organic compound having a high hole-transport property or a structure in which a substance having a donor property is added to an organic compound having a high electron-transport property. Alternatively, both of these structures may be stacked.

In the case of the structure in which a substance having an acceptor property is added to an organic compound having a high hole-transport property, as the organic compound having a high hole-transport property, for example, an aromatic amine compound such as NPB, TPD, TDATA, MTDATA, or BSPB, or the like can be used. The substances described here are mainly substances having a hole mobility of $10^{-6}$ cm$^2$Ns or higher. However, other substances may also be used as long as their hole-transport properties are higher than their electron-transport properties.

As the substance having an acceptor property, $F_4$-TCNQ, chloranil, or the like can be used. Moreover, an oxide of any of metals belonging to Groups 4 to 8 of the periodic table can be used. Specifically, it is preferable to use vanadium oxide, niobium oxide, tantalum oxide, chromium oxide, molybdenum oxide, tungsten oxide, manganese oxide, or rhenium oxide because of their high electron accepting properties. In particular, molybdenum oxide is preferable because it is stable in the air, has a low hygroscopic property, and is easy to handle.

On the other hand, in the case of the structure in which a substance having a donor property is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$, can be used. Alternatively, in addition to such a metal complex, PBD, OXD-7, TAZ, Bphen, BCP, or the like can be used. The substances described here are mainly substances having an electron mobility of $10^{-6}$ cm$^2$/Vs or higher. However, other substances may also be used as long as their electron-transport properties are higher than their hole-transport properties.

As the substance having a donor property, it is possible to use an alkali metal, a rare earth metal, a metal belonging to Group 2 or 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may also be used as the substance having a donor property.

By forming the charge-generation layer 205 with any of the above materials, it is possible to suppress an increase in driving voltage caused when the EL layers are stacked.

Figure 2B:
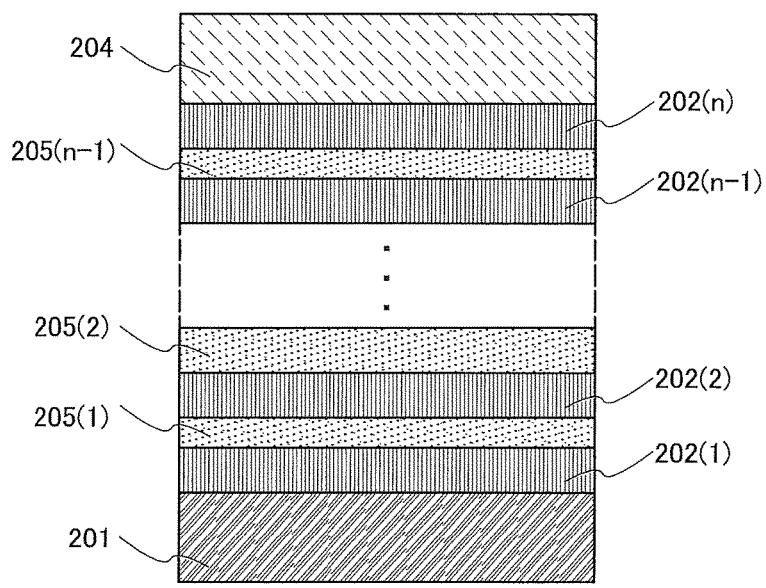

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are provided between a pair of electrodes, by providing charge-generation layers (205(1) to 205(n−1)) between the EL layers, light emission in a high luminance region can be obtained with current density kept low. Since the current density can be kept low, the element can have a long lifetime. When the light-emitting element is applied to a light-emitting device, an electronic device, a lighting device, and the like each having a large light-emitting area, uniform light emission in a large area is possible since voltage drop due to resistance of an electrode material can be reduced.

When the EL layers have different emission colors, a desired emission color can be obtained from the light-emitting element as a whole. For example, in the light-emitting element including two EL layers, when the emission color of a first EL layer and the emission color of a second EL layer are made to be complementary colors, the light-emitting element can emit white light as a whole. Note that "complementary color" means a relation between colors which become an achromatic color when they are mixed. In other words, when lights which are complementary to each other are mixed, white light emission can be obtained.

A light-emitting element including three EL layers can also emit white light as a whole, when the emission color of a first EL layer is red, the emission color of a second EL layer is green, and the emission color of a third EL layer is blue, for example.

Note that the structure described in this embodiment can be combined with any of the structures described in the other embodiments, as appropriate.

Embodiment 4

In this embodiment, a light-emitting device including a light-emitting element in which the organometallic complex of one embodiment of the present invention is used for an EL layer is described.

The light-emitting device may be either a passive matrix light-emitting device or an active matrix light-emitting device. Any of the light-emitting elements described in the other embodiments can be used for the light-emitting device described in this embodiment.

In this embodiment, an active matrix light-emitting device is first described with reference to FIGS. 3A to 3C.

Figure 3A:
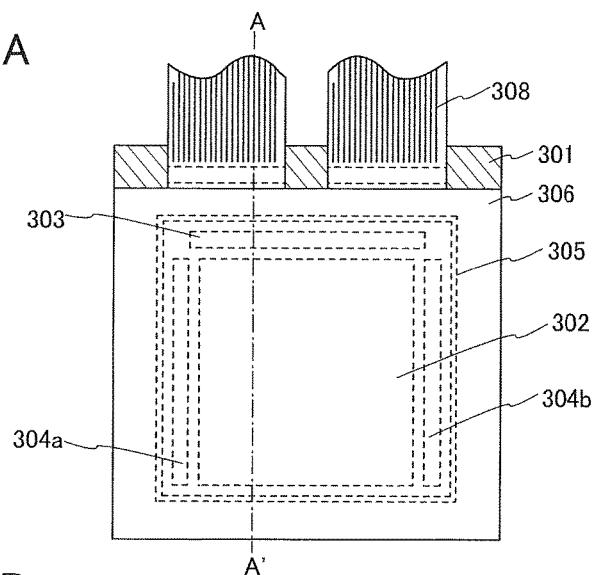
FIGS. 3A to 3C illustrate a light-emitting device.
Figure 3B:
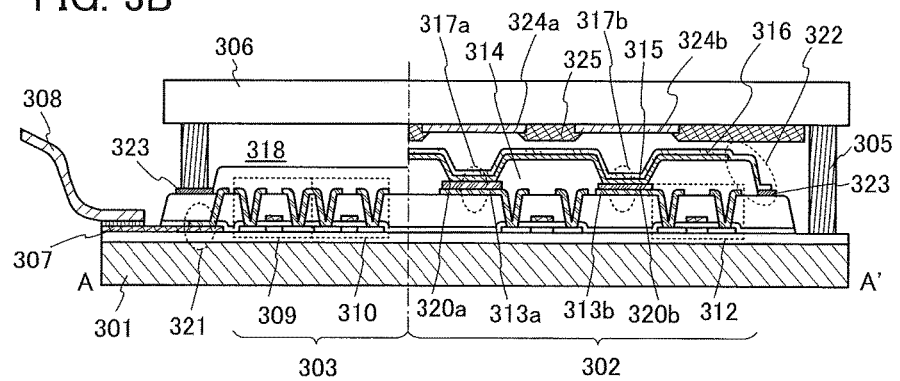

Note that FIG. 3A is a top view illustrating the light-emitting device and FIG. 3B is a cross-sectional view taken along the chain line A-A' in FIG. 3A. The active matrix light-emitting device of this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal is provided, through which a signal (e.g., a video signal, a clock signal, a start signal, a reset signal, or the like) or potential from the outside is transmitted to the driver circuit portion 303 and the driver circuit portions 304a and 304b. Here is shown an example in which an FPC 308 is provided as the external input terminal. Although only the FPC is shown here, the FPC may be provided with a printed wiring board (PWB). The light-emitting device in this specification includes not only a main body of the light-emitting device but also a light-emitting device with an FPC or a PWB attached.

Next, a cross-sectional structure is described with reference to FIG. 3B. The driver circuit portions and the pixel portion are formed over the element substrate 301; here are illustrated the driver circuit portion 303 which is the source line driver circuit and the pixel portion 302.

In the driver circuit portion 303, an FET 309 and an FET 310 are combined as an example. Note that the driver circuit portion 303 including the FET 309 and the FET 310 may be formed with a circuit including transistors having the same conductivity type (either n-channel transistors or p-channel transistors) or a CMOS circuit including an n-channel transistor and a p-channel transistor. Although a driver integrated type in which the driver circuit is formed over the substrate is described in this embodiment, the driver circuit is not necessarily formed over the substrate and can be formed outside, not over the substrate.

The pixel portion 302 includes a switching FET (not shown) and a current control FET 312, and a wiring (source or drain electrode) of the current control FET 312 is electrically connected to first electrodes (anodes) (313a and 313b) of light-emitting elements 317a and 317b. Although the pixel portion 302 includes two FETs (the switching FET and the current control FET 312) per one light-emitting element in this embodiment, the present invention is not limited thereto. Three or more FETs and a capacitor may be provided for each light-emitting element.

As the FETs 309, 310, and 312, for example, a staggered transistor or an inverted staggered transistor can be used. Examples of a semiconductor material that can be used for the FETs 309, 310, and 312 include semiconductors belonging to Group 13 of the periodic table, semiconductors belonging to Group 14 of the periodic table (e.g., silicon), compound semiconductors, oxide semiconductors, and organic semiconductor materials. In addition, there is no particular limitation on the crystallinity of the semiconductor material, and an amorphous semiconductor film or a crystalline semiconductor film can be used, for example. In particular, an oxide semiconductor is preferably used for the FETs 309, 310, and 312. Examples of the oxide semiconductor include an In—Ga oxide and an In-M-Zn oxide (M represents Al, Ga, Y, Zr, La, Ce, or Nd). For example, an oxide semiconductor material that has an energy gap of 2 eV or more, preferably 2.5 eV or more, more preferably 3 eV or more is used for the FETs 309, 310, and 312, so that the off-state current of the transistors can be reduced.

In addition, a conductive film for optical adjustment may be stacked over the first electrode 313. For example, as illustrated in FIG. 3B, the wavelengths of light extracted from the light-emitting elements 317a and 317b are different from each other; thus, conductive films 320a and 320b are formed so that the thicknesses thereof are different from each other. A partition 314 formed of an insulating material is formed so as to cover edge portions of the first electrode 313 and the conductive films 320a and 320b. In this embodiment, the partition 314 is formed using a positive photosensitive acrylic resin. In this embodiment, the first electrode 313 is used as an anode.

The partition 314 preferably has a curved surface with curvature at its upper end portion or lower end portion. This enables the coverage with a film formed over the partition 314 to be favorable. The partition 314 can be formed using, for example, either a negative photosensitive resin or a positive photosensitive resin. The material of the partition 314 is not limited to an organic compound, and an inorganic compound such as silicon oxide, silicon oxynitride, or silicon nitride can be used.

Light-emitting elements 317a and 317b each have a stacked-layer structure including the first electrode 313, an EL layer 315, and a second electrode 316, and the EL layer 315 includes at least a light-emitting layer. Furthermore, in the EL layer 315, a hole-injection layer, a hole-transport layer, an electron-transport layer, an electron-injection layer, a charge-generation layer, and the like can be provided as appropriate in addition to the light-emitting layer.

For the first electrode 313, the EL layer 315, and the second electrode 316, any of the materials given in Embodiment 2 can be used. Although not illustrated, the second electrode 316 is electrically connected to the FPC 308 which is an external input terminal. The first electrode 313 is electrically connected, through the driver circuit portion 303, to a lead wiring 307 in a region 321, and an external signal is input to the first electrode 313a through an FPC 308. Furthermore, the second electrode 316 is electrically connected to a lead wiring 323 in a region 322, and an external signal is input to the second electrode 316 through the FPC 308 although it is not shown.

Although the cross-sectional view of FIG. 3B illustrates only two light-emitting elements 317a and 317b, a plurality of light-emitting elements are arranged in a matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, any of light-emitting elements that emit light of white (W), yellow (Y), magenta (M), cyan (C), and the like may be formed. For example, when any of the light-emitting elements that emit light of a plurality of kinds of colors is used in combination with the light-emitting elements that emit light of three kinds of colors (R, G, and B), effects such as an improvement in color purity and a reduction in power consumption can be obtained. Furthermore, the light-emitting device may have an improved emission efficiency and a reduced power consumption by combination with quantum dots. Note that a separate coloring formation method may be employed in which materials different according to the emission colors or the like of the light-emitting elements are used to form light-emitting layers; alternatively, a method may be employed in which the plurality of light-emitting elements share one light-emitting layer formed using the same material and further include color filters.

The sealing substrate 306 is attached to the element substrate 301 with the sealant 305, so that the light-emitting elements 317a and 317b are provided in a space 318 surrounded by the element substrate 301, the sealing substrate 306, and the sealant 305. Color filters 324a and 324b may be provided for the sealing substrate 306, and a black layer (a black matrix) 325 is provided between adjacent color filters. Light emission obtained from the light-emitting elements 317a and 317b is extracted to the outside through the color filters 324a and 324b, respectively.

The space 318 may be filled with an inert gas (such as nitrogen or argon) or the sealant 305. In the case where the sealant is applied and then the substrates are attached, UV treatment, heat treatment, or a combination thereof is preferably performed.

An epoxy-based resin or glass frit is preferably used for the sealant 305. Such a material preferably allows as little moisture and oxygen as possible to penetrate. As the sealing substrate 306, a glass substrate, a quartz substrate, or a plastic substrate formed of fiber reinforced plastic (FRP), polyvinyl fluoride (PVF), polyester, acrylic, or the like can be used. In the case where glass frit is used as the sealant, the element substrate 301 and the sealing substrate 306 are preferably glass substrates in terms of adhesion.

In this manner, the active matrix light-emitting device can be obtained.

The light-emitting device including the light-emitting element in which the organometallic complex of one embodiment of the present invention is used for the EL layer may be a passive matrix light-emitting device, as well as the above-described active matrix light-emitting device.

Figure 3C:
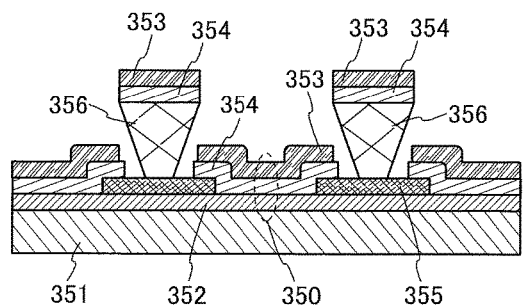

FIG. 3C is a cross-sectional view illustrating a pixel portion in a passive matrix light-emitting device.

As illustrated in FIG. 3C, a light-emitting element 350 including a first electrode 352, an EL layer 354, and a second electrode 353 is formed over a substrate 351. Note that a plurality of first electrodes 352 having an island shape are formed in one direction to form a striped pattern. In addition, an insulating film 355 is formed over the first electrodes 352 to cover end portions of the first electrodes 352.

A partition 356 formed using an insulating material is provided over the insulating film 355. The sidewalls of the partition 356 slope so that the distance between the sidewalls is gradually narrowed toward the surface of the substrate. In other words, a cross section taken along the direction of the short side of the partition 356 is trapezoidal, and the lower side (a side which is in the same direction as a plane direction of the insulating film 355 and in contact with the insulating film 355) is shorter than the upper side (a side which is in the same direction as the plane direction of the insulating film 355 and not in contact with the insulating film 355). The partition 356 thus provided can prevent defects in the light-emitting element due to static electricity or the like. Note that the insulating film 355 has an opening over part of the first electrode 352, and when the EL layer 354 is formed after formation of the partition 356, the EL layer 354 that is in contact with the first electrode 352 in the opening is formed.

After the formation of the EL layer 354, the second electrode 353 is formed. Thus, without contact with the first electrode 352, the second electrode 353 is formed over the EL layer 354 and might also be formed over the insulating film 355. Since the EL layer 354 and the second electrode 353 are formed after the formation of the partition 356, the EL layer 354 and the second electrode 353 are also sequentially stacked over the partition 356.

Note that sealing can be performed as in the case of the active matrix light-emitting device and is thus not described here.

In this manner, the passive matrix light-emitting device can be obtained.

The type of the element substrate 301 is not limited to a certain type. Examples of the substrate include a semiconductor substrate (e.g., a single crystal substrate or a silicon substrate), an SOI substrate, a glass substrate, a quartz substrate, a plastic substrate, a metal substrate such as a stainless steel substrate or a tungsten substrate, and a flexible substrate such as a laminate film, paper containing a fibrous material, or a base material film. Examples of the glass substrate include a barium borosilicate glass substrate, an aluminoborosilicate glass substrate, and a soda lime glass substrate. Examples of the flexible substrate include substrates formed of plastics typified by polyethylene terephthalate (PET), polyethylene naphthalate (PEN), polyether sulfone (PES), polytetrafluoroethylene (PTFE), polypropylene, polyester, polyvinyl fluoride, polyvinyl chloride, polyamide, polyimide, aramid, or an epoxy resin; a synthetic resin such as an acrylic resin; an inorganic film formed by evaporation; and paper.

The use of a semiconductor substrate, a single crystal substrate, an SOI substrate, or the like enables the manufacture of small-sized transistors with a small variation in characteristics, size, shape, or the like. A circuit using such transistors achieves lower power consumption or higher integration.

In the case where any of the above-described flexible substrates is used as the element substrate 301, a light-emitting element or a transistor may be provided directly over the flexible substrate. Alternatively, part of or the entire light-emitting element or transistor may be formed over a base substrate with a separation layer provided therebetween and separated from the base substrate and transferred to a flexible substrate. When the light-emitting element or the transistor is transferred to another substrate by using a separation layer as described above, the transistor or the light-emitting element can be formed over a substrate having low heat resistance or a flexible substrate over which the light-emitting element or the transistor is directly formed with difficulty. For the separation layer, a stack including inorganic films such as a tungsten film and a silicon oxide film, or an organic resin film of polyimide can be used, for example.

In other words, a transistor or a light-emitting element may be formed using one substrate, and then transferred to another substrate. Examples of a substrate to which a transistor or a light-emitting element is transferred include, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent characteristics or a transistor with low power consumption can be formed, a device with high durability or high heat resistance can be provided, or a reduction in weight or thickness can be achieved.

Note that the structure described in this embodiment can be combined with any of the structures described in the other embodiments, as appropriate.

Embodiment 5

In this embodiment, examples of a variety of electronic devices manufactured using a light-emitting device which is one embodiment of the present invention are described.

Examples of the electronic device using the light-emitting device include television devices (also referred to as TV or television receivers), monitors for computers and the like, cameras such as digital cameras and digital video cameras, digital photo frames, mobile phones (also referred to cellular phones or mobile phone devices), portable game machines, portable information terminals, audio playback devices, and stationary game machines such as pin-ball machines. Specific examples of such electronic devices are illustrated in FIGS. 4A to 4D, 4D-1, and 4D-2 and FIGS. 5A to 5C. An electronic device including a light-emitting device can also be used for an automobile windshield or an automobile dashboard. An automobile which is one embodiment of the present invention is illustrated in FIG. 6.

Figure 4A:
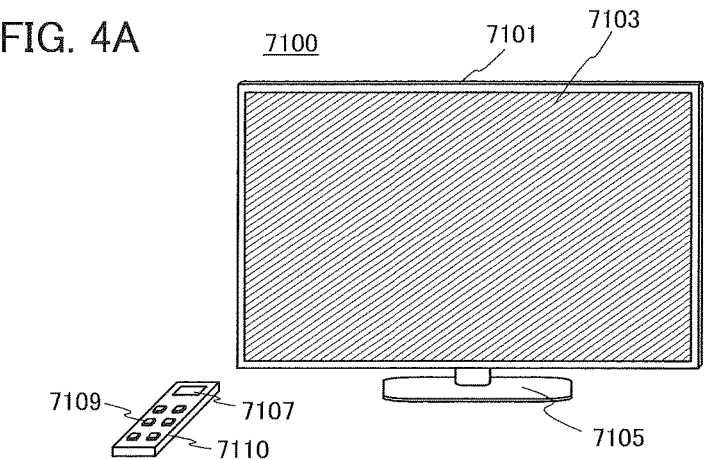
FIGS. 4A to 4D, 4D-1, and 4D-2 illustrate electronic devices.

FIG. 4A illustrates an example of a television device. In a television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 may be provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) data communication can be performed.

Figure 4B:
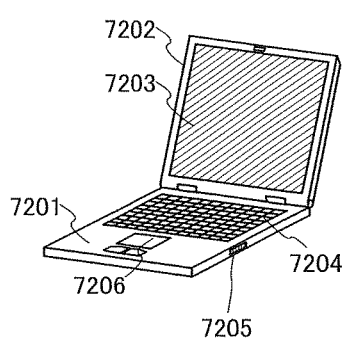

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 4C:
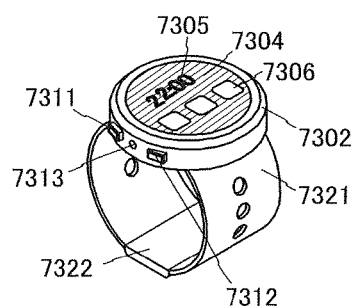

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 4C can have a variety of functions, for example, a function of displaying a variety of data (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7302 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. Note that the smart watch can be manufactured using the light-emitting device for the display panel 7304.

Figure 4D:
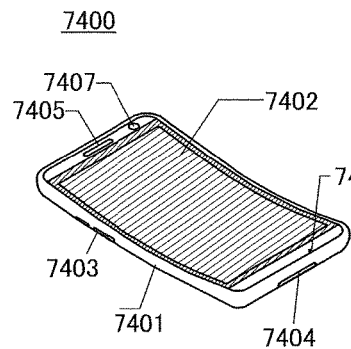

FIG. 4D illustrates an example of a mobile phone (e.g., smartphone). A mobile phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming the light-emitting element of one embodiment of the present invention over a flexible substrate, the light-emitting device can be used for the display portion 7402 with a curved surface as illustrated in FIG. 4D.

When the display portion 7402 of the mobile phone 7400 illustrated in FIG. 4D is touched with a finger or the like, data can be input to the mobile phone 7400. Furthermore, operations such as making a call and creating an e-mail can be performed by touching the display portion 7402 with a finger or the like.

There are mainly three screen modes for the display portion 7402. The first mode is a display mode mainly for displaying an image. The second mode is an input mode mainly for inputting data such as text. The third mode is a display-and-input mode in which two modes, the display mode and the input mode, are combined.

For example, in the case of making a call or creating an e-mail, a text input mode mainly for inputting text is selected for the display portion 7402 so that text displayed on the screen can be input. In that case, it is preferable to display a keyboard or number buttons on almost the entire screen of the display portion 7402.

When a detection device such as a gyroscope or an acceleration sensor is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touch on the display portion 7402 or operation with the operation button 7403 of the housing 7401. The screen modes can also be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

If an optical sensor in the display portion 7402 judges that the input by touch on the display portion 7402 is not performed for a certain period in the input mode, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Furthermore, when a backlight or a sensing light source which emits near-infrared light is provided in the display portion, an image of a finger vein, a palm vein, or the like can be taken.

Figures 1, 2, 4D:
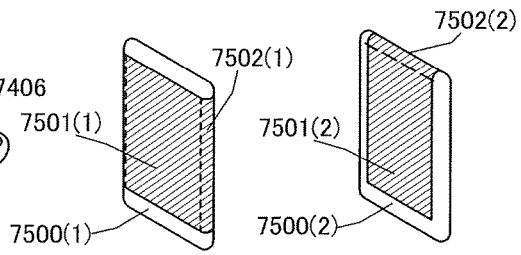

The light-emitting device of one embodiment of the present invention can also be used for a mobile phone having a structure illustrated in FIG. 4D-1 or 4D-2, which is another structure of the mobile phone (e.g., smartphone).

In the case of the structure illustrated in FIG. 4D-1 or 4D-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the mobile phone is placed in user's breast pocket.

Figure 5A:
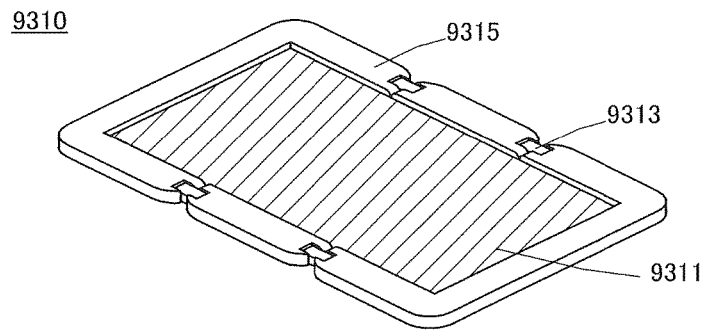
FIGS. 5A to 5C illustrate an electronic device.
Figure 5B:
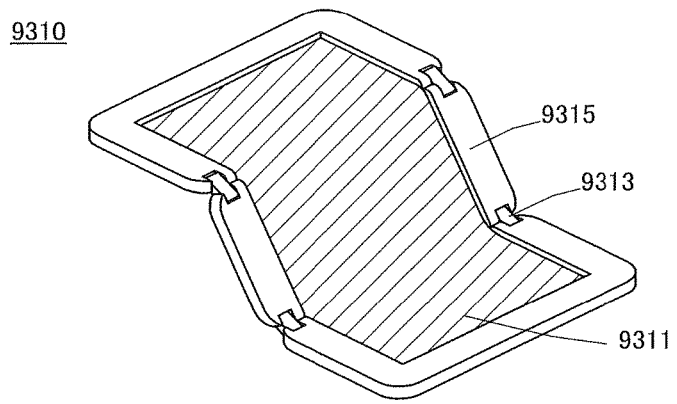
Figure 5C:
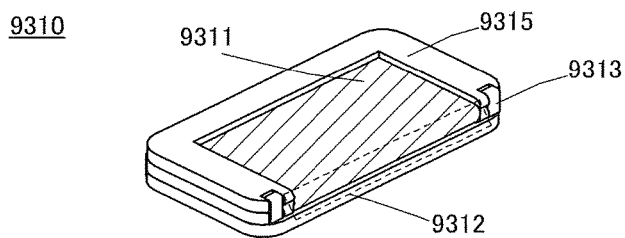
Figure 6:
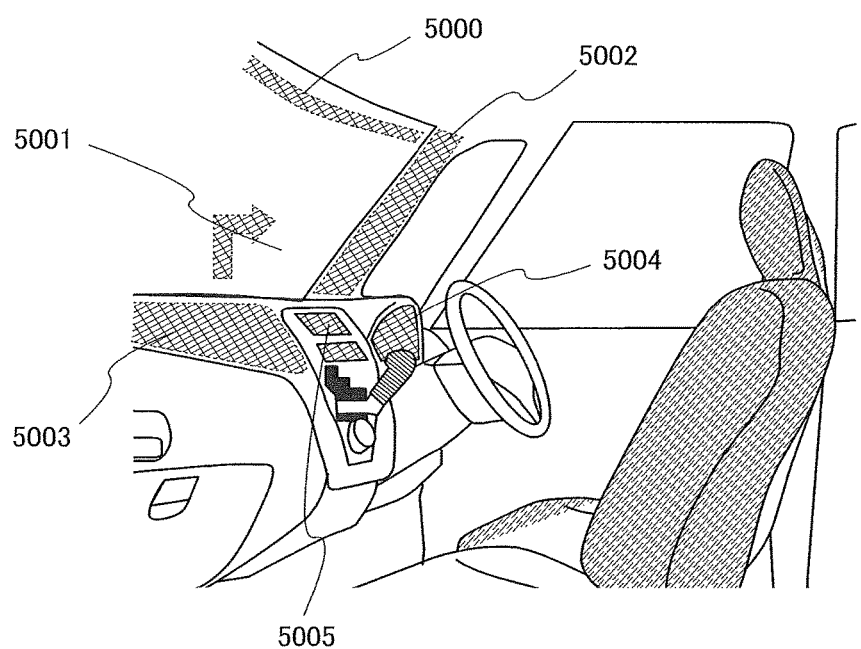
FIG. 6 illustrates in-vehicle display devices.

FIGS. 5A to 5C illustrate a foldable portable information terminal 9310. FIG. 5A illustrates the portable information terminal 9310 that is opened. FIG. 5B illustrates the portable information terminal 9310 that is being opened or being folded. FIG. 5C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. The light-emitting device of one embodiment of the present invention can be used for the display panel 9311. A display region 9312 in the display panel 9311 is a display region that is positioned at the side surface of the portable information terminal 9310 that is folded. On the display region 9312, information icons, file shortcuts of frequently used applications or programs, and the like can be displayed, and confirmation of information and start of application can be smoothly performed.

The light-emitting element containing the organic compound described in Embodiment 1 can also be used for an automobile windshield or an automobile dashboard. FIG. 6 illustrates one mode in which the light-emitting element described in Embodiment 2 is used for an automobile windshield and an automobile dashboard. Display regions 5000 to 5005 each include the light-emitting element containing the organic compound described in Embodiment 1.

The display region 5000 and the display region 5001 are display devices provided in the automobile windshield in which the light-emitting elements each containing the organic compound described in Embodiment 1 are incorporated. The light-emitting elements each containing the organic compound described in Embodiment 1 can be formed into what is called a see-through display device, through which the opposite side can be seen, by including a first electrode and a second electrode formed of electrodes having a light-transmitting property. Such see-through display devices can be provided even in the automobile windshield, without hindering the vision. Note that in the case where a driving transistor or the like is provided, a transistor having a light-transmitting property, such as an organic transistor using an organic semiconductor material or a transistor using an oxide semiconductor, is preferably used.

The display region 5002 is a display device provided in a pillar portion in which the light-emitting elements each containing the organic compound described in Embodiment 1 are incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedmeter, a tachometer, a mileage, a fuel level, a gearshift state, and air-condition setting. The content or layout of the display can be freely changed by a user as appropriate. Note that such information can also be shown by the display regions 5000 to 5003. The display regions 5000 to 5005 can also be used as lighting devices.

As described above, the electronic devices can be obtained using the light-emitting device which is one embodiment of the present invention. Note that the light-emitting device can be used for electronic devices in a variety of fields without being limited to the electronic devices described in this embodiment.

Note that the structure described in this embodiment can be combined as appropriate with any of the structures described in other embodiments.

Embodiment 6

In this embodiment, a structure of a lighting device fabricated using the light-emitting element which is one embodiment of the present invention is described with reference to FIGS. 7A to 7D.

Figure 7A:
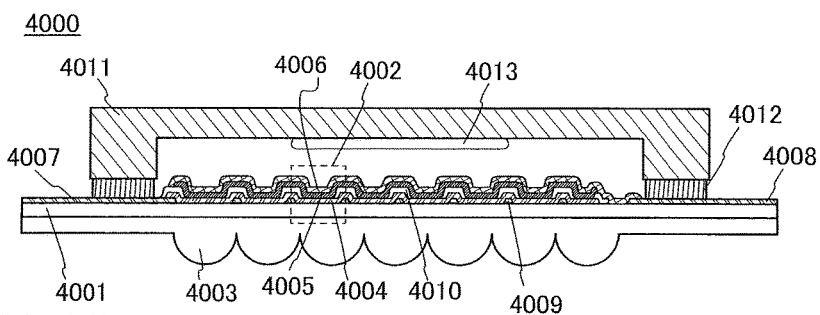
FIGS. 7A to 7D each illustrate a lighting device.
Figure 7B:
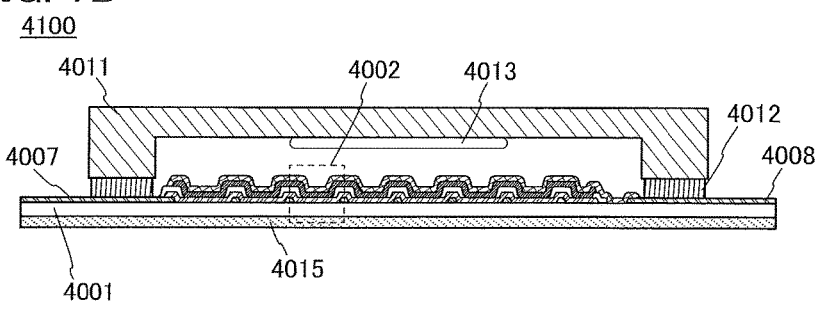
Figure 7C:
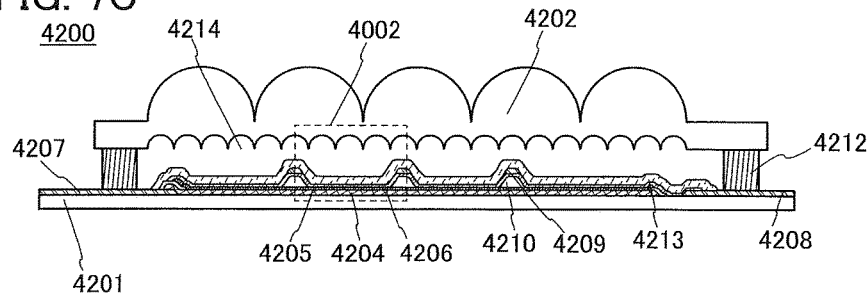
Figure 7D:
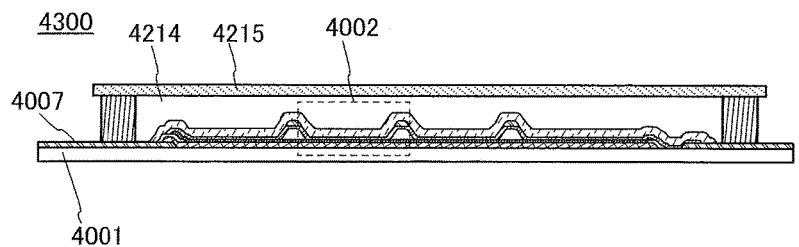

FIGS. 7A to 7D are examples of cross-sectional views of lighting devices. FIGS. 7A and 7B illustrate bottom-emission lighting devices in which light is extracted from the substrate side, and FIGS. 7C and 7D illustrate top-emission lighting devices in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 7B.

A lighting device 4200 illustrated in FIG. 7C includes the light-emitting element 4002 over a substrate 4201. The light-emitting element 4002 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4202 with unevenness are bonded to each other by a sealant 4212. A barrier film 4213 and a planarization film 4214 may be provided between the sealing substrate 4202 and the light-emitting element 4002. The sealing substrate 4202 has the unevenness illustrated in FIG. 7C, whereby the extraction efficiency of light emitted from the light-emitting element 4002 can be increased.

Instead of the sealing substrate 4202, a diffusion plate 4215 may be provided over the light-emitting element 4002 as in a lighting device 4300 illustrated in FIG. 7D.

Note that the EL layers 4005 and 4205 in this embodiment can include the organometallic complex which is one embodiment of the present invention. In that case, a lighting device with low power consumption can be provided.

Note that the structure described in this embodiment can be combined with any of the structures described in the other embodiments, as appropriate.

Embodiment 7

In this embodiment, examples of a lighting device to which the light-emitting device described in Embodiment 4 is applied are described with reference to FIG. 8.

Figure 8:
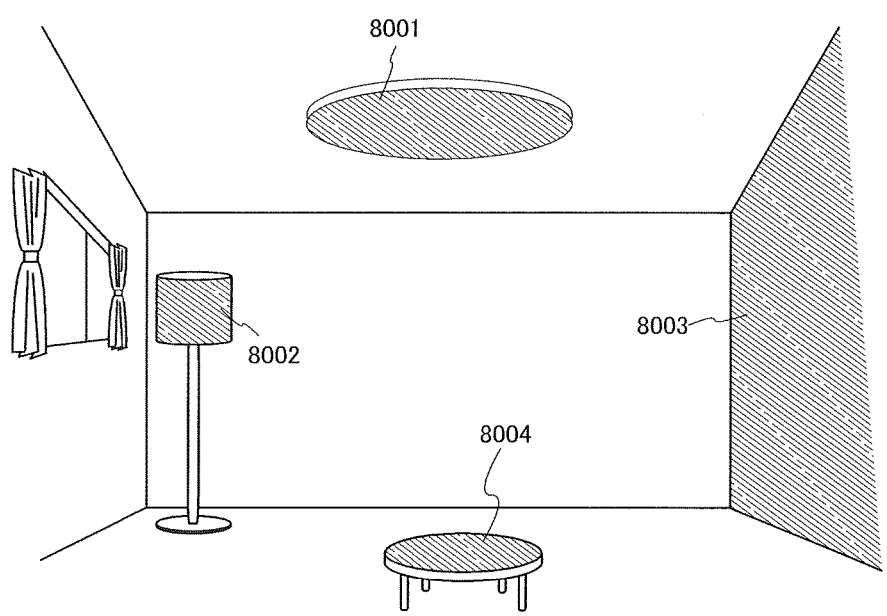
FIG. 8 illustrates lighting devices.

FIG. 8 illustrates an example in which the light-emitting device is used for an indoor lighting device 8001. Since the area of the light-emitting device can be increased, a lighting device having a large area can be formed. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Furthermore, the wall of a room may be provided with a large-sized lighting device 8003.

When the light-emitting device is used for a table by being used as the surface of the table, a lighting device 8004 which has a function of the table can be obtained. When the light-emitting device is used as part of other furniture, a lighting device which has a function of the corresponding furniture can be obtained.

In this manner, a variety of lighting devices to which the light-emitting device is applied can be obtained. Note that such lighting devices are also embodiments of the present invention.

Note that the structure described in this embodiment can be combined with any of the structures described in the other embodiments, as appropriate.

Embodiment 8

In this embodiment, a touch panel including the light-emitting element of one embodiment of the present invention or the light-emitting device of one embodiment of the present invention is described with reference to FIGS. 9A and 9B, FIGS. 10A and 10B, FIGS. 11A and 11B, FIGS. 12A and 12B, and FIG. 13.

Figure 9A:
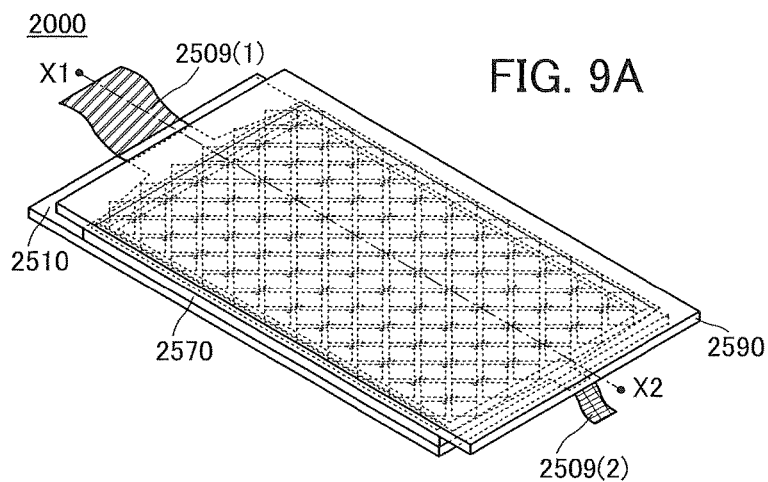
FIGS. 9A and 9B illustrate an example of a touch panel.
Figure 9B:
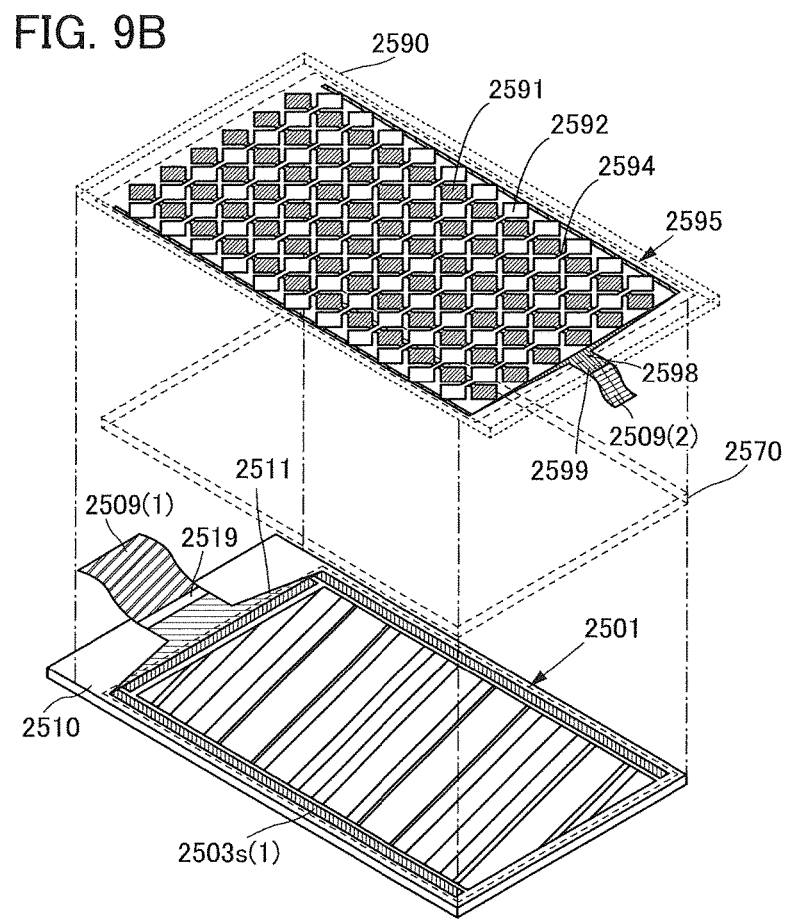

FIGS. 9A and 9B are perspective views of a touch panel 2000. Note that FIGS. 9A and 9B illustrate only main components of the touch panel 2000 for simplicity.

The touch panel 2000 includes a display portion 2501 and a touch sensor 2595 (see FIG. 9B). The touch panel 2000 further includes a substrate 2510, a substrate 2570, and a substrate 2590. Note that the substrate 2510, the substrate 2570, and the substrate 2590 each have flexibility.

The display portion 2501 includes a plurality of pixels over the substrate 2510 and a plurality of wirings 2511 through which a signal can be supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 9B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor include a surface capacitive touch sensor and a projected capacitive touch sensor.

Examples of a projected capacitive touch sensor include a self-capacitive touch sensor and a mutual capacitive touch sensor, which differ from each other mainly in the driving method. The use of a mutual capacitive touch sensor is preferable because multiple points can be sensed simultaneously.

First, an example of using a projected capacitive touch sensor is described with reference to FIG. 9B. Note that in the case of a projected capacitive touch sensor, a variety of sensors that can sense the approach or contact of an object such as a finger can be used.

The touch sensor 2595 as the projected capacitive sensor includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction as illustrated in FIGS. 9A and 9B. In the same manner, the electrodes 2591 each have a shape of a plurality of quadrangles arranged in one direction with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle of greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, variation in luminance of light passing through the touch sensor 2595 can be reduced.

Note that the shapes of the electrodes 2591 and the electrodes 2592 are not limited to the above-mentioned shapes and can be any of a variety of shapes. For example, a plurality of electrodes 2591 may be provided so that a space between the electrodes 2591 is reduced as much as possible, and a plurality of electrodes 2592 may be provided with an insulating layer provided between the electrodes 2591 and the electrodes 2592. In that case, between two adjacent electrodes 2592, it is preferable to provide a dummy electrode which is electrically insulated from these electrodes, because the area of a region having a different transmittance can be reduced.

Figure 10A:
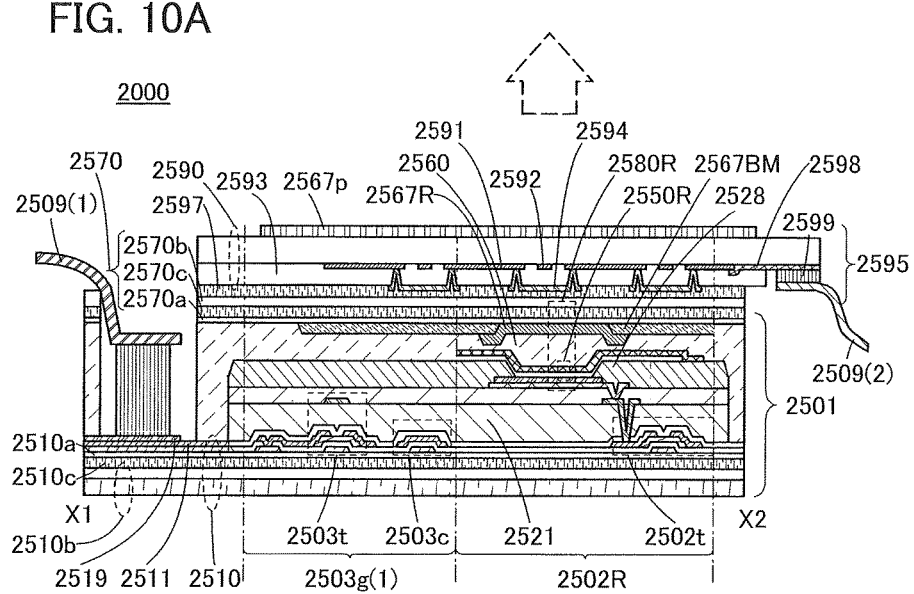
FIGS. 10A and 10B illustrate the example of a touch panel.
Figure 10B:
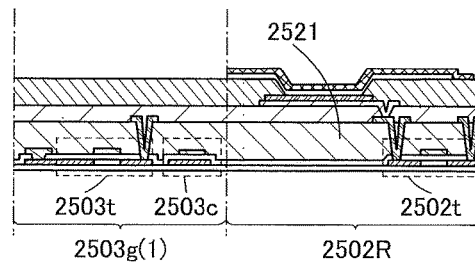

Next, the touch panel 2000 is described in detail with reference to FIGS. 10A and 10B. FIGS. 10A and 10B are cross-sectional views taken along the dashed-dotted line X1-X2 in FIG. 9A.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

An adhesive layer 2597 is provided under the wiring 2594. The substrate 2590 is attached to the substrate 2570 with the adhesive layer 2597 so that the touch sensor 2595 overlaps with the display portion 2501.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film including graphene oxide. As a reducing method, a method using heat or the like can be employed.

For example, the electrodes 2591 and the electrodes 2592 can be formed by depositing a light-transmitting conductive material on the substrate 2590 by a sputtering method and then removing an unnecessary portion by any of various patterning techniques such as a photolithography method.

Examples of a material used for the insulating layer 2593 include a resin such as acrylic or epoxy, a resin having a siloxane bond, and an inorganic insulating material such as silicon oxide, silicon oxynitride, or aluminum oxide.

The wiring 2594 is formed in an opening provided in the insulating layer 2593, whereby the adjacent electrodes 2591 are electrically connected to each other. A light-transmitting conductive material can be favorably used for the wiring 2594 because the aperture ratio of the touch panel can be increased. Moreover, a material having higher conductivity than the electrodes 2591 and 2592 can be favorably used for the wiring 2594 because electric resistance can be reduced.

Through the wiring 2594, a pair of electrodes 2591 are electrically connected to each other. Between the pair of electrodes 2591, the electrode 2592 is provided.

The wiring 2598 is electrically connected to any of the electrodes 2591 and 2592. Part of the wiring 2598 serves as a terminal. For the wiring 2598, for example, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display portion 2501 includes a plurality of pixels arranged in a matrix. Each of the pixels includes a display element and a pixel circuit for driving the display element.

For the substrate 2510 and the substrate 2570, for example, a flexible material having a vapor permeability of $10^{-5}$ g/(m$^2$·day) or lower, preferably $10^{-6}$ g/(m$^2$·day) or lower can be favorably used. Note that materials whose thermal expansion coefficients are substantially equal to each other are preferably used for the substrates 2510 and 2570. For example, the coefficients of linear expansion of the materials are preferably $1\times10^{-3}$/K or lower, more preferably $5\times10^{-5}$/K or lower, still more preferably $1\times10^{-5}$/K or lower.

A sealing layer 2560 preferably has a higher refractive index than the air. In the case where light is extracted to the sealing layer 2560 side as illustrated in FIG. 10A, the sealing layer 2560 can also serve as an optical element.

The display portion 2501 includes a pixel 2502R. The pixel 2502R includes a light-emitting module 2580R.

The pixel 2502R includes a light-emitting element 2550R and a transistor 2502t which can supply power to the light-emitting element 2550R. Note that the transistor 2502t functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode.

In the case where the sealing layer 2560 is provided on the light extraction side, the sealing layer 2560 is in contact with the light-emitting element 2550R and the coloring layer 2567R.

The coloring layer 2567R overlaps with the light-emitting element 2550R. Accordingly, part of light emitted from the light-emitting element 2550R passes through the coloring layer 2567R and is emitted to the outside of the light-emitting module 2580R as indicated by the arrow in the figure.

The display portion 2501 includes a light-blocking layer 2567BM on the light extraction side. The light-blocking layer 2567BM is provided so as to surround the coloring layer 2567R.

The display portion 2501 includes an anti-reflective layer 2567p in a region that overlaps with the pixels. As the anti-reflective layer 2567p, a circular polarizing plate can be used, for example.

An insulating layer 2521 is provided in the display portion 2501. The insulating layer 2521 covers the transistor 2502t. Note that the insulating layer 2521 has a function of covering the roughness caused by the pixel circuit to provide a flat surface. The insulating layer 2521 may have a function of suppressing diffusion of impurities. This can prevent a reduction in reliability of the transistor 2502t or the like due to diffusion of impurities.

The light-emitting element 2550R is formed over the insulating layer 2521. A partition 2528 is provided so as to overlap with an end portion of the lower electrode in the light-emitting element 2550R. Note that a spacer for controlling the distance between the substrate 2510 and the substrate 2570 may be provided over the partition 2528.

A scan line driver circuit 2503g(1) includes a transistor 2503t and a capacitor 2503c. Note that the driver circuit can be formed in the same process and over the same substrate as those of the pixel circuit.

Over the substrate 2510, the wirings 2511 through which a signal can be supplied are provided. Over the wirings 2511, the terminal 2519 is provided. The FPC 2509(1) is electrically connected to the terminal 2519. The FPC 2509(1) has a function of supplying signals such as an image signal and a synchronization signal. Note that a printed wiring board (PWB) may be attached to the FPC 2509(1).

For the display portion 2501, a transistor with any of a variety of structures can be used. In the example illustrated in FIG. 10A, a bottom-gate transistor is used. In each of the transistor 2502t and the transistor 2503t illustrated in FIG. 10A, a semiconductor layer including an oxide semiconductor can be used for a channel region. Alternatively, in each of the transistor 2502t and the transistor 2503t, a semiconductor layer including amorphous silicon can be used for a channel region. Further alternatively, in each of the transistor 2502t and the transistor 2503t, a semiconductor layer including polycrystalline silicon which is obtained by a crystallization process such as laser annealing can be used for a channel region.

FIG. 10B illustrates the structure of the display portion 2501 in which a top-gate transistor is used.

In the case of a top-gate transistor, as well as the above semiconductor layers that can be used for a bottom-gate transistor, a semiconductor layer including a film that is transferred from a polycrystalline silicon substrate or a single crystal silicon substrate or the like may be used for a channel region.

Next, a touch panel having a structure different from that illustrated in FIGS. 10A and 10B is described with reference to FIGS. 11A and 11B.

Figure 11A:
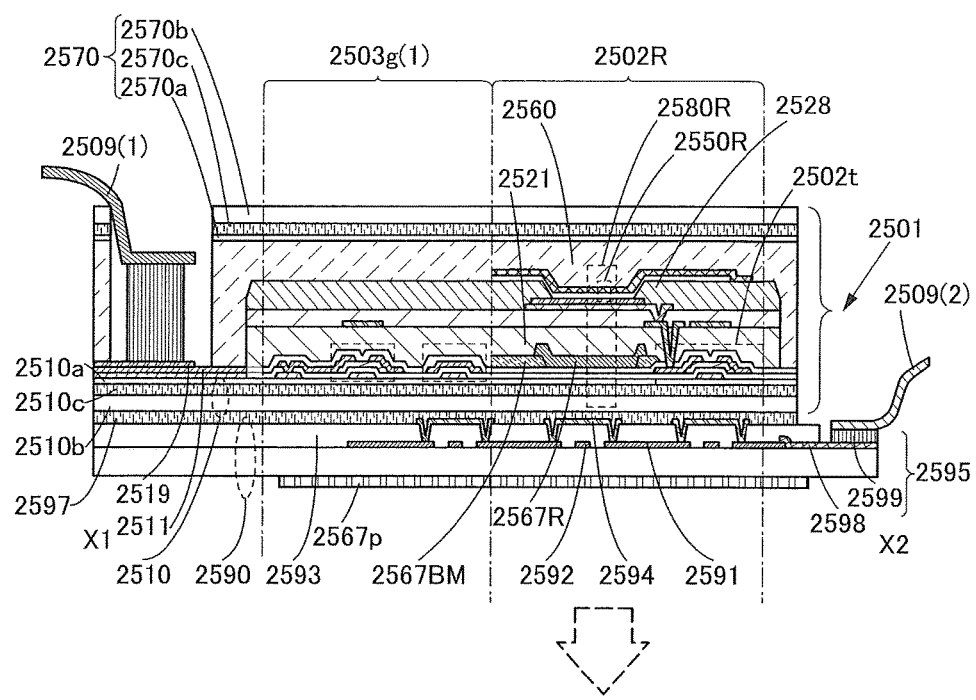
FIGS. 11A and 11B illustrate an example of a touch panel.
Figure 11B:
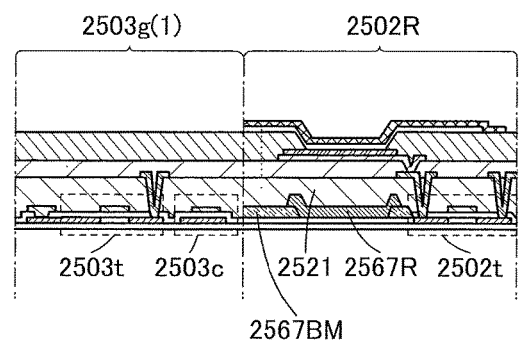

FIGS. 11A and 11B are cross-sectional views of a touch panel 2001. The touch panel 2001 illustrated in FIGS. 11A and 11B differs from the touch panel 2000 illustrated in FIGS. 10A and 10B in the position of the touch sensor 2595 relative to the display portion 2501. Different structures are described in detail below, and the above description of the touch panel 2000 can be referred to for the other structures.

The coloring layer 2567R overlaps with the light-emitting element 2550R. The light-emitting element 2550R illustrated in FIG. 11A emits light to the side where the transistor 2502t is provided. Accordingly, part of light emitted from the light-emitting element 2550R passes through the coloring layer 2567R and is emitted to the outside of the light-emitting module 2580R as indicated by the arrow in the figure.

The display portion 2501 includes the light-blocking layer 2567BM on the light extraction side. The light-blocking layer 2567BM is provided so as to surround the coloring layer 2567R.

The touch sensor 2595 is provided on the substrate 2510 side of the display portion 2501 (see FIG. 11A).

The display portion 2501 and the touch sensor 2595 are attached to each other with the adhesive layer 2597 provided between the substrate 2510 and the substrate 2590.

In the display portion 2501, a transistor with any of a variety of structures can be used. In the example illustrated in FIG. 11A, a bottom-gate transistor is used. In the example illustrated in FIG. 11B, a top-gate transistor is used.

Next, an example of a method of driving a touch panel is described with reference to FIGS. 12A and 12B.

Figure 12A:
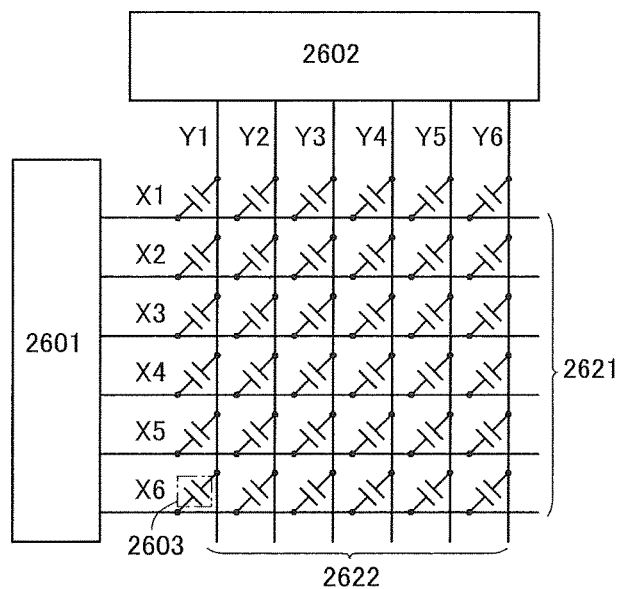
FIGS. 12A and 12B are a block diagram and a timing chart, respectively, of a touch sensor.

FIG. 12A is a block diagram showing the configuration of a mutual capacitive touch sensor. FIG. 12A shows a pulse voltage output circuit 2601 and a current sensing circuit 2602. Note that in FIG. 12A, six wirings X1 to X6 represent electrodes 2621 to which a pulse voltage is applied, and six wirings Y1 to Y6 represent electrodes 2622 that sense changes in current. FIG. 12A also shows capacitors 2603 which are each formed in a region where the electrodes 2621 and 2622 overlap with each other. Note that functional replacement between the electrodes 2621 and 2622 is possible.

The pulse voltage output circuit 2601 is a circuit for sequentially applying a pulse to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in mutual capacitance in the capacitor 2603. The approach or contact of an object can be sensed by utilizing this change.

The current sensing circuit 2602 is a circuit for sensing changes in current flowing through the wirings Y1 to Y6 which are caused by the change in mutual capacitance in the capacitor 2603. No change in current value is sensed in the wirings Y1 to Y6 when there is no approach or contact of an object, whereas a decrease in current value is sensed when mutual capacitance is decreased owing to the approach or contact of an object. Note that an integrator circuit or the like is used for sensing of current values.

Figure 12B:
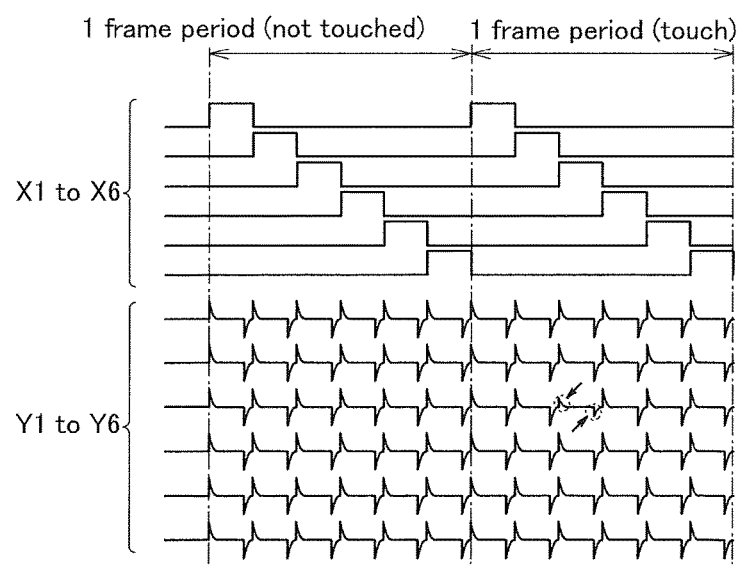

FIG. 12B is a timing chart showing input and output waveforms in the mutual capacitive touch sensor shown in FIG. 12A. In FIG. 12B, sensing of an object is performed in all the rows and columns in one frame period. FIG. 12B shows a period during which an object is not sensed (not touched) and a period during which an object is sensed (touched). Sensed current values of the wirings Y1 to Y6 are shown as the waveforms of voltage values.

A pulse voltage is sequentially applied to the wirings X1 to X6, and waveforms of the wirings Y1 to Y6 change in accordance with the pulse voltage. When there is no approach or contact of an object, the waveforms of the wirings Y1 to Y6 change in accordance with changes in the voltages of the wirings X1 to X6. The current value is decreased at the point of approach or contact of an object and accordingly the waveform of the voltage value changes. By sensing a change in mutual capacitance in this manner, the approach or contact of an object can be sensed.

Figure 13:
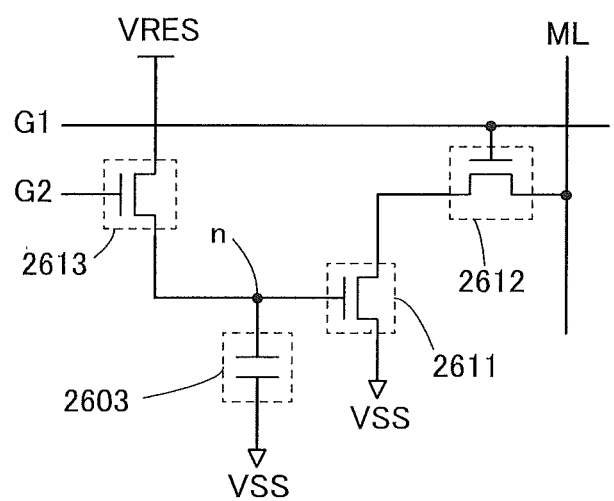
FIG. 13 is a circuit diagram of a touch sensor.

Although FIG. 12A shows a passive matrix touch sensor in which only the capacitor 2603 is provided at the intersection of wirings as a touch sensor, an active matrix touch sensor including a transistor and a capacitor may also be used. FIG. 13 shows an example of a sensor circuit included in an active matrix touch sensor.

The sensor circuit shown in FIG. 13 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is supplied to a gate of the transistor 2612, and a wiring ML is electrically connected to the other of the source and the drain of the transistor 2612. A voltage VSS is applied to the other electrode of the capacitor 2603.

Next, the operation of the sensor circuit shown in FIG. 13 is described. First, a potential for turning on the transistor 2613 is supplied as the signal G2, and a potential corresponding to the voltage VRES is applied to a node n connected to the gate of the transistor 2611. Then, a potential for turning off the transistor 2613 is supplied as the signal G2, so that the potential of the node n is held. Then, mutual capacitance of the capacitor 2603 changes owing to the approach or contact of an object such as a finger, and accordingly the potential of the node n changes from VRES.

In reading operation, a potential for turning on the transistor 2612 is supplied as the signal G1. A current flowing through the transistor 2611, that is, a current flowing through the wiring ML changes in accordance with the potential of the node n. By sensing this current, the approach or contact of an object can be sensed.

In each of the transistors 2611, 2612, and 2613, an oxide semiconductor layer is preferably used as a semiconductor layer in which a channel region is formed. In particular, such a transistor is used as the transistor 2613, so that the potential of the node n can be held for a long time and the frequency of operation of resupplying VRES to the node n (refresh operation) can be reduced.

At least part of this embodiment can be implemented in combination with any of the other embodiments described in this specification, as appropriate.

Example 1

Synthesis Example 1

In this example, a method of synthesizing bis[2-(5-ethyl-5H-4-pyrimido[5,4-b]indolyl-κN3)phenyl-κC](2,4-pentanedionato-κ²O,O')iridium(III) (abbreviation: [Ir(pidrpm)$_2$(acac)]), which is an organometallic complex of one embodiment of the present invention and represented by the structural formula (100) in Embodiment 1, is described. The structure of [Ir(pidrpm)$_2$(acac)] is shown below.

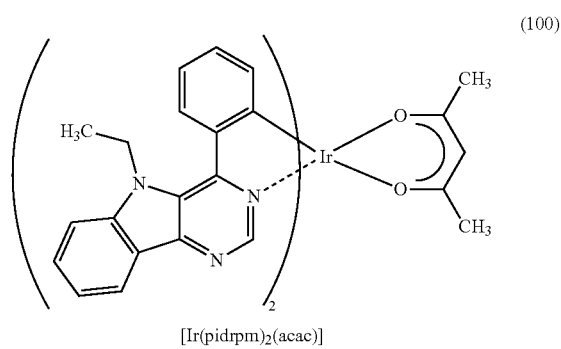

[Ir(pidrpm)$_2$(acac)]

Step 1: Synthesis of 4-phenyl-5H-pyrimido[5,4-b]indole

First, 1.00 g of 4-chloro-5H-pyrimido[5,4-b]indole, 0.90 g of phenylboronic acid, 0.78 g of sodium carbonate, 0.020 g of bis(triphenylphosphine)palladium(II) dichloride (abbreviation: Pd(PPh$_3$)$_2$Cl$_2$), 20 mL of water, and 20 mL of DMF were put into a recovery flask equipped with a reflux pipe, and the air in the flask was replaced with argon. This reaction container was heated by irradiation with microwaves (2.45 GHz, 100 W) for 1 hour. After that, water was added to this reaction solution and an organic layer was extracted with dichloromethane. The extracted solution was washed with saturated brine, and dried with magnesium sulfate. The solution obtained by the drying was filtered. The solvent of this filtrate was distilled off, and then the obtained residue was purified by silica gel column chromatography using ethyl acetate as a developing solvent, so that 4-phenyl-5H-pyrimido[5,4-b]indole, which was the desired pyrimidine derivative, was obtained as a yellowish white powder in a yield of 75%. Note that the irradiation with microwaves was performed using a microwave synthesis system (Discover, manufactured by CEM Corporation). The synthesis scheme of the step 1 is shown in (A-1) below.

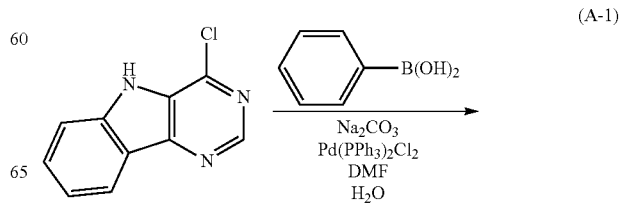

-continued

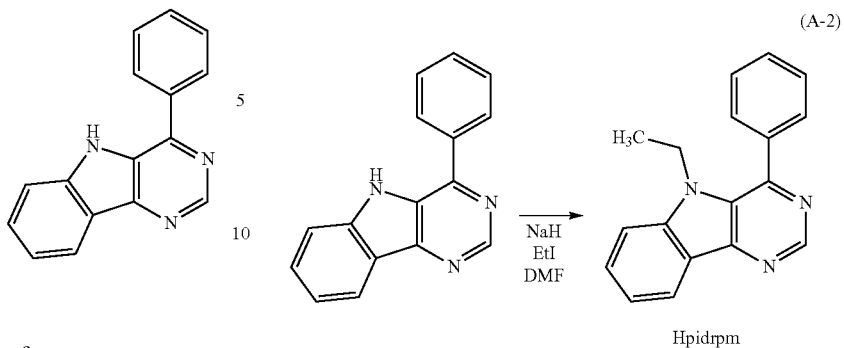

(A-2)

Hpidrpm

Step 2: Synthesis of 5-ethyl-4-phenylpyrimido[5,4-b]indole (abbreviation: Hpidrpm)

Next, 0.89 g of 4-phenyl-5H-pyrimido[5,4-b]indole obtained in the above step 1 and 0.18 mL of dry DMF were put into a 100-mL three-neck flask and the air in the flask was replaced with nitrogen. Then, sodium hydride (60% dispersion in paraffin liquid, 0.44 g) was added to this mixture, and the mixture was stirred at room temperature for 30 minutes. Further, 0.58 mL of iodoethane was added dropwise, and the mixture was stirred at room temperature for 18 hours. Then, 100 mL of water was poured into the obtained reaction solution, and the precipitated solid was collected by suction filtration. The obtained solid was purified by silica gel column chromatography using ethyl acetate as a developing solvent, so that Hpidrpm, which was the desired pyrimidine derivative, was obtained as a yellowish white powder in a yield of 78%. The synthesis scheme of the step 2 is shown in (A-2) below.

Step 3: Synthesis of di-μ-chloro-tetrakis[2-(5-ethyl-5H-4-pyrimido[5,4-b]indolyl-κN3)phenyl-κC]di-iridium(III) (abbreviation: [Ir(pidrpm)$_2$Cl]$_2$)

Next, into a recovery flask equipped with a reflux pipe were put 15 mL of 2-ethoxyethanol, 5 mL of water, 0.91 g of Hpidrpm obtained in the above step 2, and 0.48 g of iridium chloride hydrate (IrCl$_3$.H$_2$O) (produced by Heraeus K.K.), and the air in the flask was replaced with argon. After that, irradiation with microwaves (2.45 GHz, 100 W) was performed for 1 hour to cause a reaction. After the solvent of this reaction solution was distilled off, methanol was added to the obtained residue, and the mixture was washed with methanol to give [Ir(pidrpm)$_2$Cl]$_2$, which is a dinuclear complex, as a reddish brown powder in a yield of 78%. The synthesis scheme of the step 3 is shown in (A-3) below.

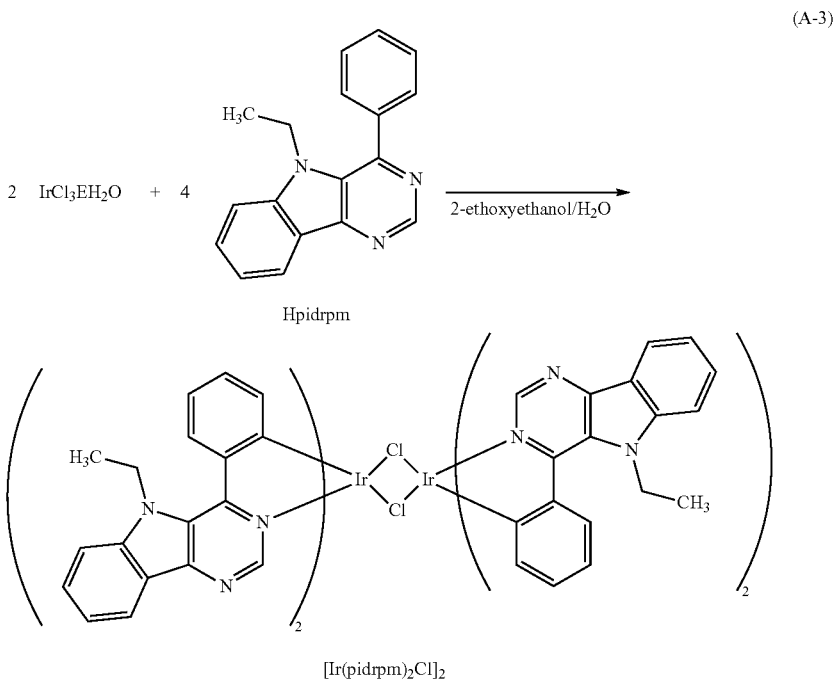

(A-3)

[Ir(pidrpm)$_2$Cl]$_2$

Step 4: Synthesis of bis[2(5-ethyl-5H-4-pyrimido[5,4-b]indolyl-κN3)phenyl-κC](2,4-pentanedionato-κ$^2$O,O')iridium(III) (abbreviation: [Ir(pidrpm)$_2$(acac)]

Next, into a recovery flask equipped with a reflux pipe were put 20 mL of 2-ethoxyethanol, 0.97 g of [Ir(pidrpm)

$_2$Cl]$_2$, which was the dinuclear complex obtained in the above step 3, 0.19 g of acetylacetone (abbreviation: Hacac), and 0.67 g of sodium carbonate, and the air in the flask was replaced with argon. Then, irradiation with microwaves (2.45 GHz, 100 W) was performed for 60 minutes. Here, 0.19 g of Hacac was added, and irradiation with microwaves (2.45 GHz, 100 W) was performed again for 60 minutes so that heating was performed. The solvent of this reaction solution was distilled off, and methanol was added to the obtained residue and this mixture was suction-filtered. The obtained solid was washed with water and methanol. After the obtained solid was purified by flash column chromatography using hexane and ethyl acetate as a developing solvent in a ratio of 2:1, recrystallization was carried out with a mixed solvent of dichloromethane and methanol; thus, [Ir(pidrpm)$_2$(acac)], which is the organometallic complex of one embodiment of the present invention, was obtained as a red powder in a yield of 56%. By a train sublimation method, 0.48 g of the obtained red powder was purified. In the purification by sublimation, the solid was heated at 285° C. under a pressure of 2.7 Pa with an argon flow rate of 5 mL/min After the purification by sublimation, a red solid of the desired substance was obtained in a yield of 83%. The synthesis scheme of the step 4 is shown in (A-4).

Figure 15:
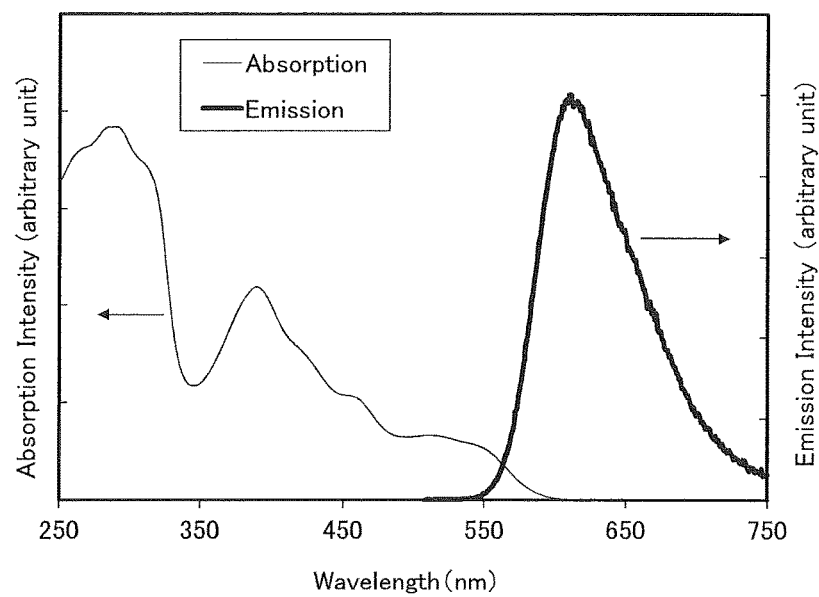
FIG. 15 shows an ultraviolet-visible absorption spectrum and an emission spectrum of the organometallic complex represented by the structural formula (100).

Next, [Ir(pidrpm)$_2$(acac)] was analyzed by ultraviolet-visible (UV) absorption spectroscopy. A UV spectrum was measured with an ultraviolet-visible light spectrophotometer (manufactured by JASCO Corporation, V550 type) using a dichloromethane solution (0.092 mmol/L) at room temperature. In addition, an emission spectrum of [Ir(pidrpm)$_2$(acac)] was measured. The emission spectrum was measured with a fluorescence spectrophotometer (FS920, produced by Hamamatsu Photonics K.K.) using a degassed dichloromethane solution (0.092 mmol/L) at room temperature. The measurement results are shown in FIG. 15. The horizontal axis represents wavelength and the vertical axis represents molar absorption coefficient and emission intensity.

As shown in FIG. 15, [Ir(pidrpm)$_2$(acac)], which is the organometallic complex of one embodiment of the present invention, has an emission peak at 610 nm. Vermilion light emission was observed from the dichloromethane solution.

Next, [Ir(pidrpm)$_2$(acac)] obtained in this example was subjected to liquid chromatography mass spectrometry (LC/MS analysis).

In the LC/MS analysis, liquid chromatography (LC) was carried out with ACQUITY UPLC (registered trademark) (manufactured by Waters Corporation), and mass spectrom-

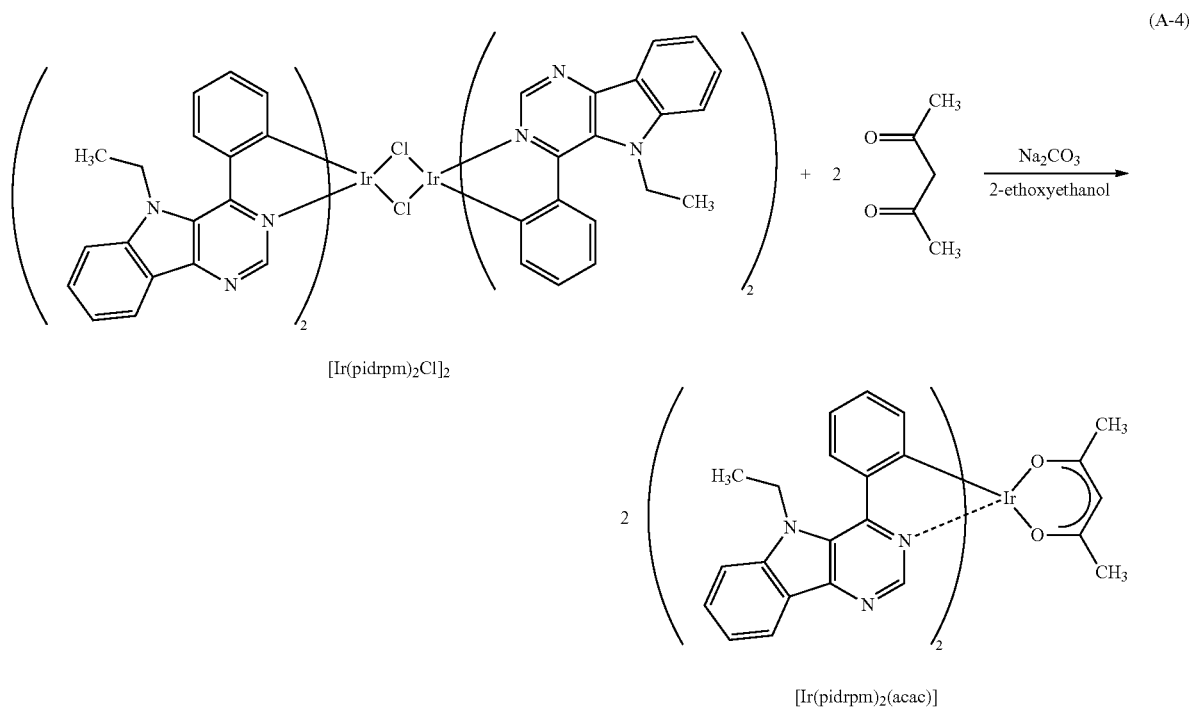

(A-4)

[Ir(pidrpm)$_2$Cl]$_2$

[Ir(pidrpm)$_2$(acac)]

Figure 14:
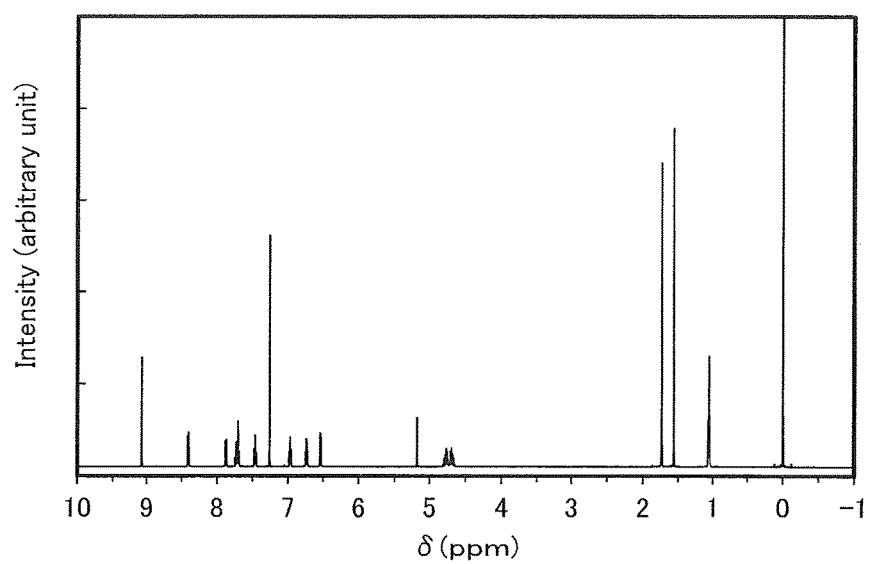
FIG. 14 is a ¹H-NMR chart of the organometallic complex represented by the structural formula (100).

Analysis results by nuclear magnetic resonance ($^1$H-NMR) spectroscopy of the red powder obtained in the above step 4 is shown below. In addition, FIG. 14 shows a $^1$H-NMR chart. The results revealed that [Ir(pidrpm)$_2$(acac)], which is the above-described organometallic complex of one embodiment of the present invention and represented by the structural formula (100), was obtained in this synthesis example.

$^1$H-NMR. δ(CDCl$_3$): 1.06 (t, 6H), 1.74 (s, 6H), 4.65-4.81 (m, 4H), 5.19 (s, 1H), 6.54 (d, 2H), 6.75 (t, 2H), 6.97 (t, 2H), 7.46 (t, 2H), 7.69-7.75 (m, 4H), 7.88 (d, 2H), 8.41 (d, 2H), 9.07 (s, 2H).

etry (MS) was carried out with Xevo G2 Tof MS (manufactured by Waters Corporation). ACQUITY UPLC (registered trademark) BEH C8 (2.1×100 mm, 1.7 μm) was used as a column for LC, and the column temperature was set to 40° C. Acetonitrile was used for Mobile Phase A, and a 0.1% formic acid aqueous solution was used for Mobile Phase B. A sample was prepared in such a manner that [Ir(pidrpm)$_2$(acac)] was dissolved in chloroform at a given concentration and the mixture was diluted with acetonitrile. The injection amount was 5.0 μL.

In LC, a gradient method in which the composition of mobile phases is changed was employed. The ratio of Mobile Phase A to Mobile Phase B was 50:50 for 0 to 1 minute after the start of the measurement, and then the composition was changed such that the ratio of Mobile Phase A to Mobile Phase B after 10 minutes was 95:5. The ratio was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. The mass range for the measurement was m/z=100 to 1200.

A component with m/z of 836.25 which underwent the separation and the ionization under the above-described conditions was collided with an argon gas in a collision cell to dissociate into product ions. Energy (collision energy) for the collision with argon was 30 eV and 70 eV. The detection results of the product ions dissociated by time-of-flight (TOF) MS are shown in FIG. 16 (at collision energy of 30 eV) and FIG. 17 (at collision energy of 70 eV).

Figure 16:
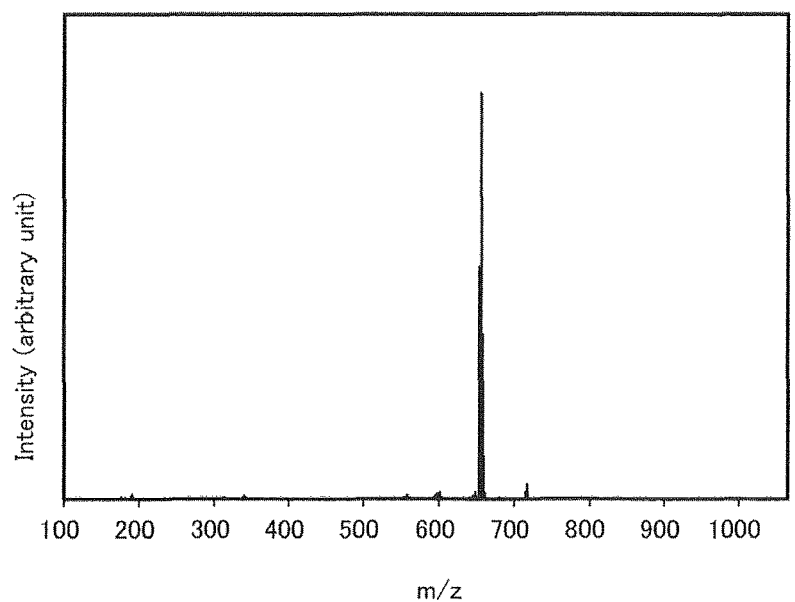
FIG. 16 shows LC/MS analysis results of the organometallic complex represented by the structural formula (100).
Figure 17:
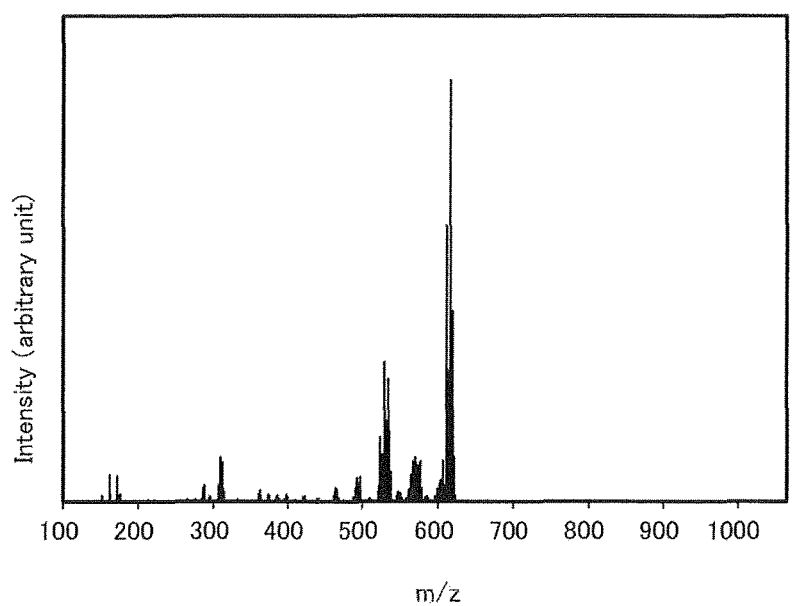
FIG. 17 shows LC/MS analysis results of the organometallic complex represented by the structural formula (100).

FIG. 16 shows that product ions of [Ir(pidpm)$_2$(acac)], which is the organometallic complex of one embodiment of the present invention represented by the structural formula (100), are mainly detected around m/z=737.20. The results in FIG. 17 show characteristics derived from [Ir(pidrpm)$_2$(acac)] and therefore can be regarded as important data for identifying [Ir(pidrpm)$_2$(acac)] contained in a mixture.

It is presumed that the product ion around m/z=737.20 is a cation in a state where acetylacetone and a proton were eliminated from the compound represented by the structural formula (100), and this is a characteristic of the organometallic complex of one embodiment of the present invention.

Example 2

Figure 18:
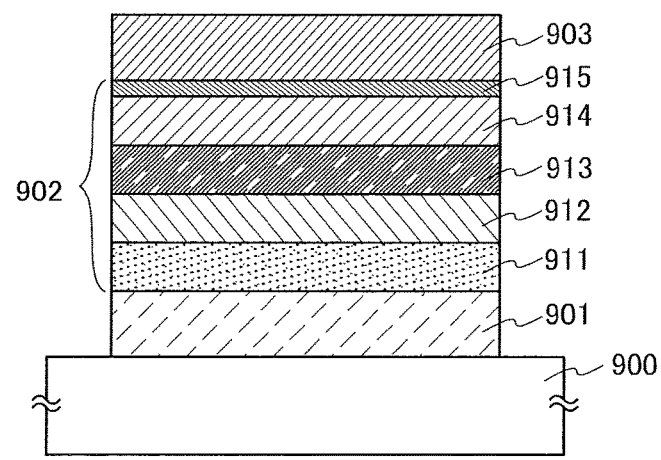
FIG. 18 illustrates a light-emitting element.

In this example, a light-emitting element 1 in which [Ir(pidrpm)$_2$(acac)], the organometallic complex of one embodiment of the present invention (structural formula (100)), is used for a light-emitting layer is described with reference to FIG. 18. Chemical formulae of materials used in this example are shown below.

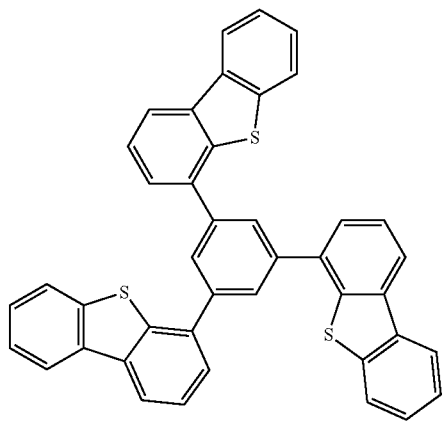

DBT3P-II

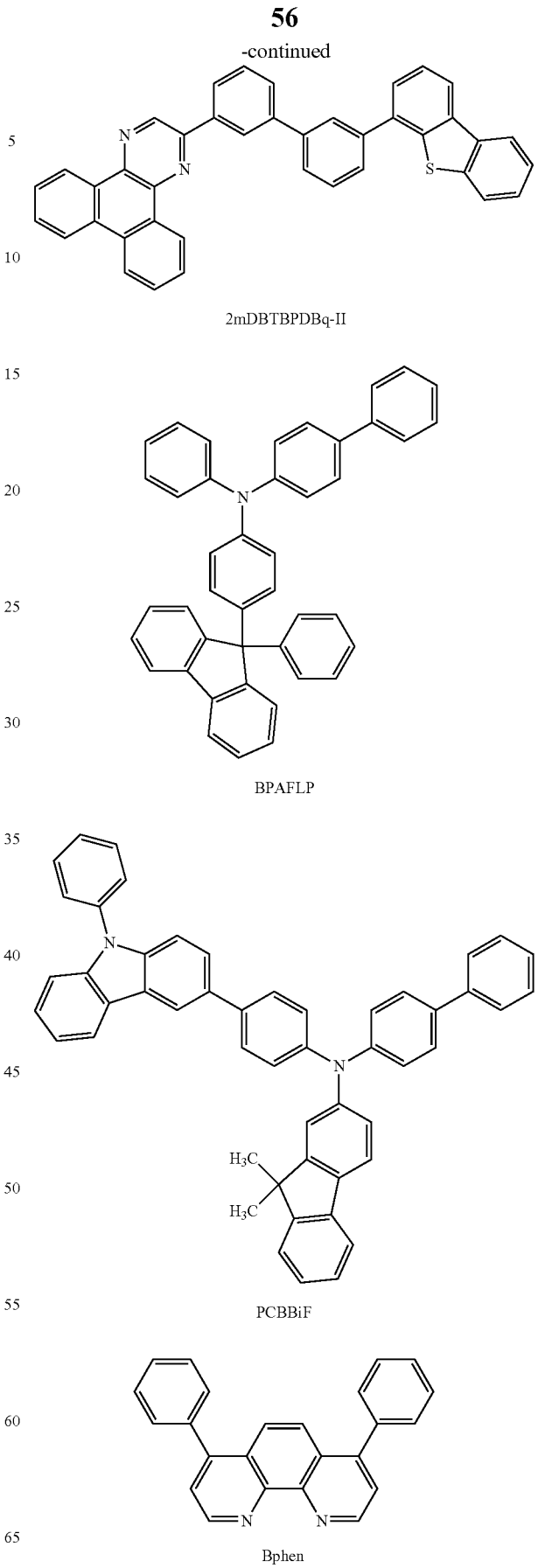

2mDBTBPDBq-II

BPAFLP

PCBBiF

Bphen

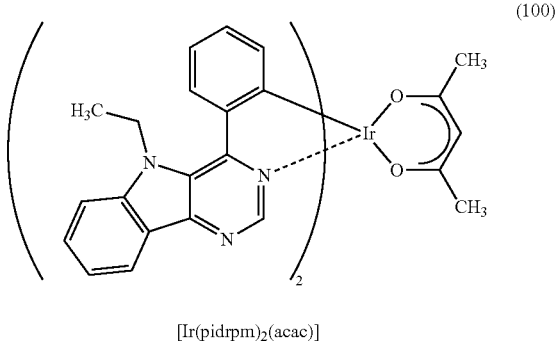

[Ir(pidrpm)₂(acac)]

<<Fabrication of Light-Emitting Element 1>>

First, indium tin oxide containing silicon oxide (ITSO) was deposited over a glass substrate 900 by a sputtering method, so that a first electrode 901 which functions as an anode was formed. Note that the thickness of the first electrode 901 was set to 110 nm and that the area of the first electrode 901 was set to 2 mm×2 mm.

Next, as pretreatment for fabricating the light-emitting element 1 over the substrate 900, a surface of the substrate was washed with water, baking was performed at 200° C. for 1 hour, and then UV ozone treatment was performed for 370 seconds.

After that, the substrate 900 was transferred into a vacuum evaporation apparatus in which the pressure had been reduced to approximately $10^{-4}$ Pa, subjected to vacuum baking at 170° C. for 30 minutes in a heating chamber of the vacuum evaporation apparatus, and then cooled down for approximately 30 minutes.

Next, the substrate 900 was fixed to a holder provided in the vacuum evaporation apparatus so that the surface of the substrate 900 over which the first electrode 901 was formed faced downward. In this example, the case is described where a hole-injection layer 911, a hole-transport layer 912, a light-emitting layer 913, an electron-transport layer 914, and an electron-injection layer 915 which are included in an EL layer 902 are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2; in this manner, the hole-injection layer 911 was formed over the first electrode 901. The thickness of the hole-injection layer 911 was set to 20 nm Note that co-evaporation is an evaporation method in which a plurality of different substances are concurrently vaporized from their respective evaporation sources.

Next, BPAFLP was deposited by evaporation to a thickness of 20 nm, whereby the hole-transport layer 912 was formed.

Next, the light-emitting layer 913 was formed over the hole-transport layer 912 by co-evaporation of 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluor en-2-amine (abbreviation: PCBBiF), and [Ir(pidrpm)₂(acac)] with a mass ratio of 2mDBTBPDBq-H to PCBBiF and [Ir(pidrpm)₂(acac)] being 0.8:0.2:0.01. The thickness of the light-emitting layer 913 was set to 40 nm.

Next, the electron-transport layer 914 was formed in such a manner that 2mDBTBPDBq-II was deposited by evaporation over the light-emitting layer 913 to a thickness of 20 nm and then Bphen was deposited by evaporation to a thickness of 10 nm. Furthermore, lithium fluoride was deposited to a thickness of 1 nm over the electron-transport layer 914 by evaporation, whereby the electron-injection layer 915 was formed.

Finally, aluminum was deposited by evaporation to a thickness of 200 nm on the electron-injection layer 915 to form a second electrode 903 serving as a cathode. In this manner, the light-emitting element 1 was fabricated. Note that in all of the above evaporation steps, evaporation was performed by a resistance-heating method.

Table 1 shows the element structure of the light-emitting element 1 fabricated as described above.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (110 nm) | DBT3P-II:MoOx (4:2 20 nm) | BPAFLP (20 nm) | * | 2mDBTBPDBq-II (20 nm) | Bphen (10 nm) | LiF (1 nm) | Al (200 nm) |

* 2mDBTBPDBq-II:PCBBiF:[Ir(pidrpm)₂(acac)] (0.8:0.2:0.01 40 nm)

The light-emitting element 1 was sealed in a glove box under a nitrogen atmosphere so as not to be exposed to the air (specifically, a sealant was applied to surround the element, and UV treatment was performed and heat treatment was performed at 80° C. for 1 hour).

<<Operation Characteristics of Light-Emitting Element 1>>

The operation characteristics of the light-emitting element 1 were measured. Note that the measurements were performed at room temperature (in an atmosphere kept at 25° C.).

Figure 19:
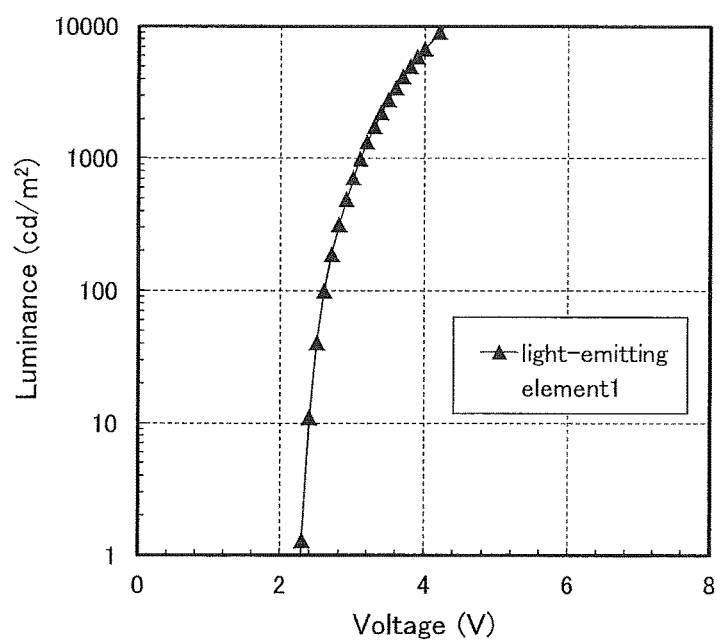
FIG. 19 shows voltage-luminance characteristics of a light-emitting element 1.
Figure 20:
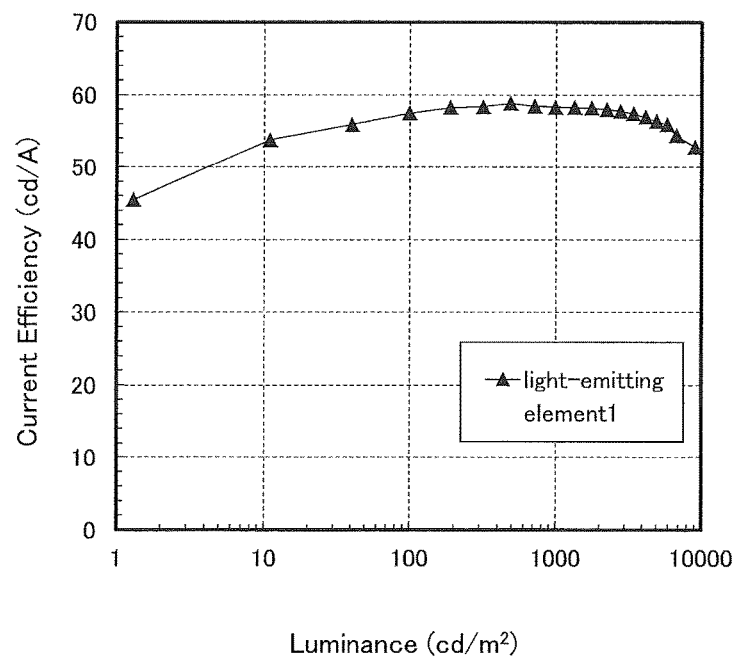
FIG. 20 shows luminance-current efficiency characteristics of the light-emitting element 1.
Figure 21:
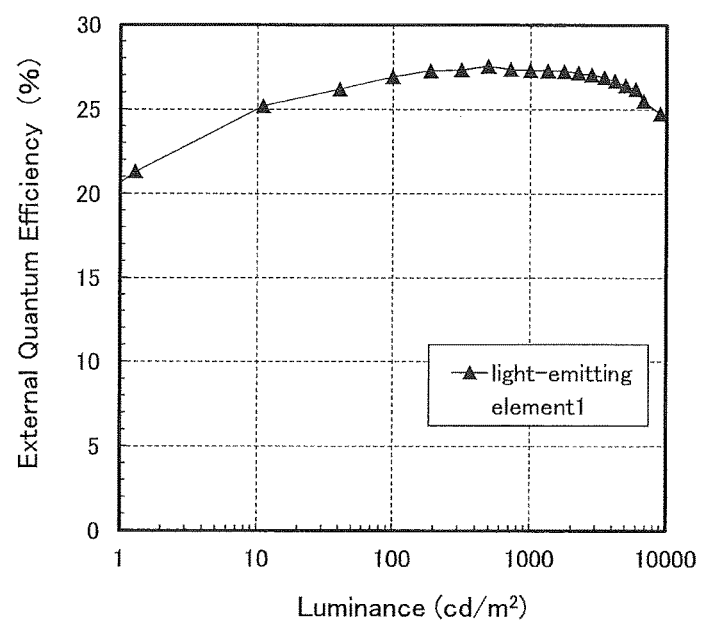
FIG. 21 shows luminance-external quantum efficiency characteristics of the light-emitting element 1.

FIG. 19 shows voltage-luminance characteristics of the light-emitting element 1. In FIG. 19, the vertical axis represents luminance (cd/m²), and the horizontal axis represents voltage (V). FIG. 20 shows luminance-current efficiency characteristics of the light-emitting element 1. In FIG. 20, the vertical axis represents current efficiency (cd/A) and the horizontal axis represents luminance (cd/m²). FIG. 21 shows luminance-external quantum efficiency characteristics of the light-emitting element 1. In FIG. 21, the vertical axis represents external quantum efficiency (%), and the horizontal axis represents luminance (cd/m²).

FIGS. 19 to 21 reveal that the light-emitting element 1 which is one embodiment of the present invention has high efficiency. Table 2 shows initial values of the main characteristics of the light-emitting element 1 at a luminance of about 1000 cd/m².

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.1 | 0.068 | 1.7 | (0.60, 0.39) | 990 | 58 | 59 | 27 |

As shown in the above results, the light-emitting element 1 emitted light with high current efficiency and high external quantum efficiency at a low drive voltage.

Figure 22:
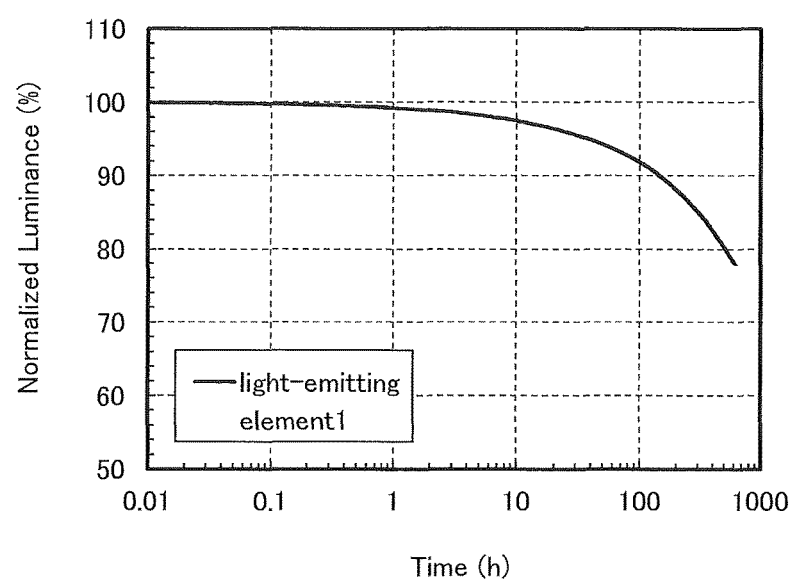
FIG. 22 shows reliability of the light-emitting element 1.

The light-emitting element 1 was subjected to a reliability test. FIG. 22 shows the results of the reliability test. In FIG. 22, the vertical axis represents normalized luminance (%) on the assumption that the initial luminance is 100%, and the horizontal axis represents driving time (h) of the element. Note that in the reliability test, the light-emitting element 1 was driven under the conditions where the initial luminance was set to 5000 cd/m$^2$ and the current density was constant. The results demonstrated that the luminance of the light-emitting element 1 after 100-hour driving was approximately 92% of the initial luminance.

Thus, the light-emitting element 1 was found to be highly reliable. In addition, it was confirmed that with the use of the organometallic complex which is one embodiment of the present invention, a light-emitting element with a long lifetime can be obtained.

Figure 23:
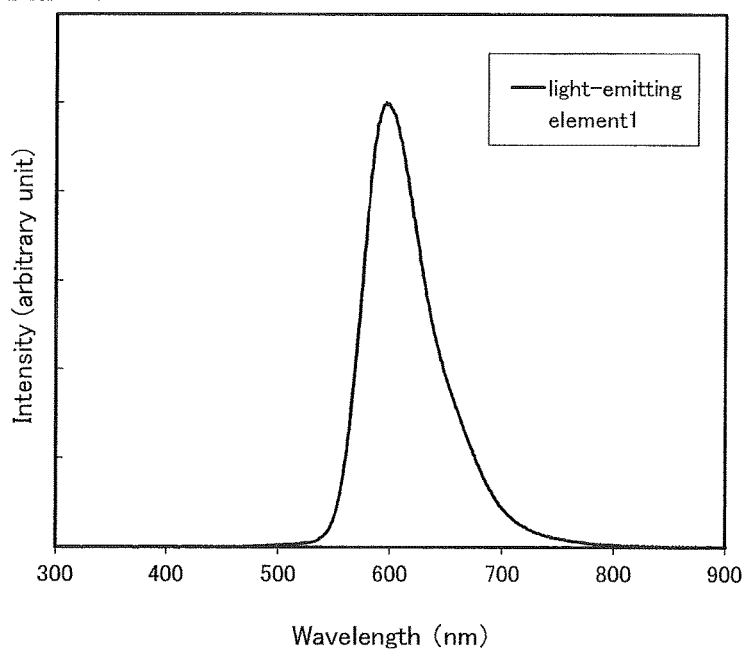
FIG. 23 shows an emission spectrum of the light-emitting element 1.

FIG. 23 shows an emission spectrum of the light-emitting element 1 to which current was applied at a current density of 2.5 mA/cm$^2$. As shown in FIG. 23, the emission spectrum of the light-emitting element 1 has a peak at around 596 nm and it is suggested that the peak is derived from emission of [Ir(pidrpm)$_2$(acac)], which is the organometallic complex of one embodiment of the present invention.

This application is based on Japanese Patent Application serial no. 2015-074799 filed with Japan Patent Office on Apr. 1, 2015, the entire contents of which are hereby incorporated by reference.

What is claimed is:

1. A light-emitting element comprising a light-emitting layer,
wherein the light-emitting layer comprises a first organic compound, a second organic compound, and an organometallic complex,
wherein the organometallic complex comprises a metal and a first ligand,
wherein the first ligand comprises a 5H-pyrimido[5,4-b]indole skeleton and an aryl group bonded to a 4-position of the 5H-pyrimido[5,4-b]indole skeleton,
wherein the metal is iridium or platinum,
wherein a 3-position of the 5H-pyrimido [5,4-b]indole skeleton and the aryl group are bonded to the metal, and
wherein a 5-position of the 5H-pyrimido[5,4-b]indole skeleton is bonded to an ethyl groups, and wherein the aryl group is a substituted phenyl group, a substituted or unsubstituted naphthyl group, or a substituted or unsubstituted fluorenyl group.

2. The light-emitting element according to claim 1, wherein the organometallic complex further comprises a second ligand,
wherein the second ligand is a monoanionic bidentate chelate ligand comprising a β-diketone structure, a carboxyl group, a phenolic hydroxyl group, or a structure in which two coordinating elements are both nitrogen, and
wherein the second ligand is bonded to the metal.

3. A light-emitting element comprising a light-emitting layer,
wherein:
the light-emitting layer comprises a first organic compound, a second organic compound, and an organometallic complex comprising a structure represented by a general formula (G1):

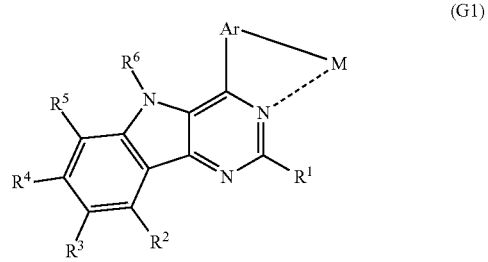

(G1)

M represents iridium or platinum;
Ar represents a substituted phenyl group, a substituted or unsubstituted naphthyl group, or a substituted or unsubstituted fluorenyl group;
each of R$^1$ to R$^5$ independently represents hydrogen, a substituted or unsubstituted alkyl group having 1 to 6 carbon atoms, or a substituted or unsubstituted aryl group having 6 to 10 carbon atoms; and
R$^6$ represents an ethyl group.

4. A light-emitting element comprising a light-emitting layer,
wherein:
the light-emitting layer comprises a first organic compound, a second organic compound, and an organometallic complex represented by a general formula (G2):

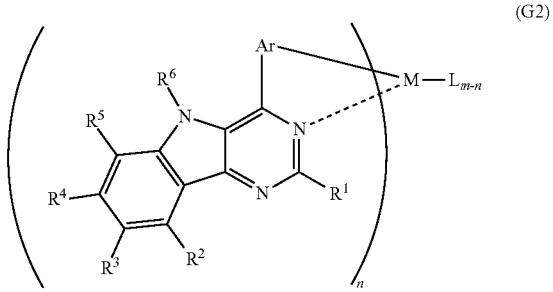

(G2)

M represents iridium or platinum;
L represents a monoanionic ligand;

Ar represents a substituted phenyl group, a substituted or unsubstituted naphthyl group, or a substituted or unsubstituted fluorenyl group;

each of $R^1$ to $R^5$ independently represents hydrogen, a substituted or unsubstituted alkyl group having 1 to 6 carbon atoms, or a substituted or unsubstituted aryl group having 6 to 10 carbon atoms;

$R^6$ represents an ethyl group;

when M represents iridium, m is 3 and n is 2 or 3; and when M represents platinum, m is 2 and n is 1 or 2.

5. The light-emitting element according to claim 4, wherein the monoanionic ligand is a monoanionic bidentate chelate ligand comprising a β-diketone structure, a monoanionic bidentate chelate ligand comprising a carboxyl group, a monoanionic bidentate chelate ligand comprising a phenolic hydroxyl group, or a monoanionic bidentate chelate ligand in which two coordinating elements are both nitrogen.

6. The light-emitting element according to claim 4, wherein:

the monoanionic ligand is represented by a general formulae (L1);

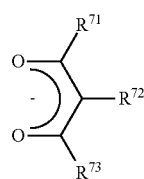

(L1)

each of $R^{71}$ to $R^{73}$ independently represents hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, or a substituted or unsubstituted alkylthio group having 1 to 6 carbon atoms.

7. The light-emitting element according to claim 4, wherein:

the organometallic complex is represented by a general formula (G3); and

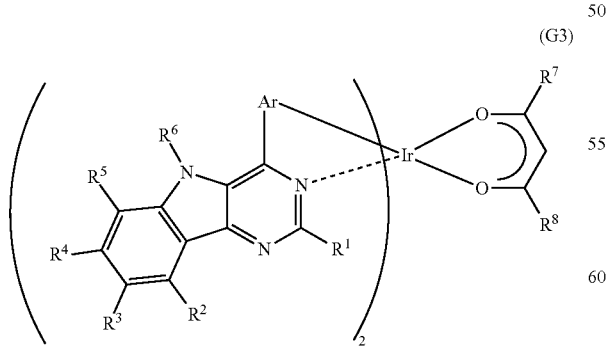

(G3)

each of $R^7$ and $R^8$ independently represents hydrogen or a substituted or unsubstituted alkyl group having 1 to 6 carbon atoms.

8. The light-emitting element according to claim 4, wherein the organometallic complex is represented by a general formula (G4),

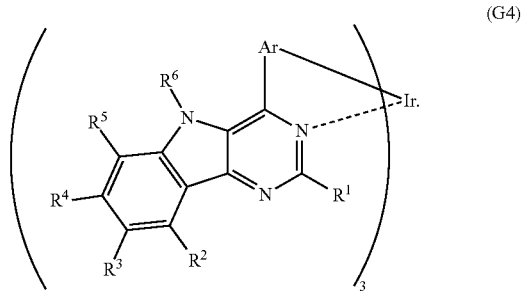

(G4)

9. The light-emitting element according to claim 4, wherein the organometallic complex is represented by a structural formula (100),

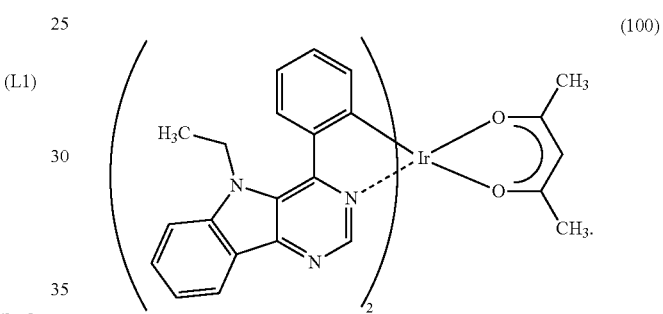

(100)

10. The light-emitting element according to claim 4, wherein the organometallic complex is represented by a structural formula (127),

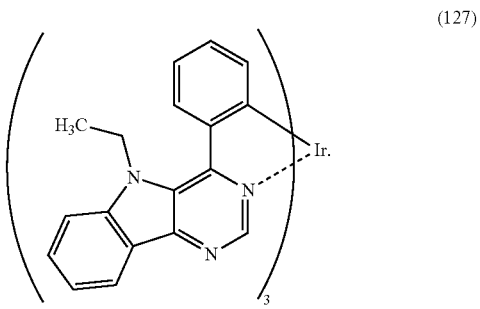

(127)

11. The light-emitting element according to claim 4, wherein the first organic compound is a carbazole derivative.

12. A light-emitting device comprising:
the light-emitting element according to claim 4; and
a transistor or a substrate.

13. An electronic device comprising:
the light-emitting device according to claim 12; and
a microphone, a camera, an operation button, an external connection portion, or a speaker.

14. A lighting device comprising:
the light-emitting device according to claim 12; and
a housing, a cover, or a support.

15. The light-emitting element according to claim 1, wherein the first organic compound is a carbazole derivative.

16. The light-emitting element according to claim 3, wherein the first organic compound is a carbazole derivative.

17. A light-emitting element comprising an organometallic complex,
- wherein the organometallic complex comprises a metal and a first ligand,
- wherein the first ligand comprises a 5H-pyrimido[5,4-b] indole skeleton and an aryl group bonded to a 4-position of the 5H-pyrimido[5,4-b]indole skeleton,
- wherein the metal is iridium or platinum,
- wherein a 3-position of the 5H-pyrimido[5,4-b]indole skeleton and the aryl group are bonded to the metal,
- wherein a 5-position of the 5H-pyrimido[5,4-b]indole skeleton is bonded to an ethyl group, and
- wherein the aryl group is a substituted phenyl group, a substituted or unsubstituted naphthyl group, or a substituted or unsubstituted fluorenyl group.

18. The light-emitting element according to claim 17,
- wherein the organometallic complex further comprises a second ligand,
- wherein the second ligand is a monoanionic bidentate chelate ligand comprising a β-diketone structure, a carboxyl group, a phenolic hydroxyl group, or a structure in which two coordinating elements are both nitrogen, and
- wherein the second ligand is bonded to the metal.

* * * * *